US011672849B2

United States Patent
Eaton et al.

(10) Patent No.: US 11,672,849 B2
(45) Date of Patent: Jun. 13, 2023

(54) METHOD OF INHIBITING LUNG OR BREAST CANCER GROWTH WITH ENGINEERED EMBRYONIC STEM-CELL DERIVED EXOSOMES COMPOSITIONS

(71) Applicant: University of Louisville Research Foundation, Inc., Louisville, KY (US)

(72) Inventors: John W. Eaton, Prospect, KY (US); Kavitha Yaddanapudi, Louisville, KY (US); Chi Li, Louisville, KY (US)

(73) Assignee: University of Louisville Research Foundation, Inc., Louisville, KY (US)

( * ) Notice: Subject to any disclaimer, the term of this patent is extended or adjusted under 35 U.S.C. 154(b) by 352 days.

(21) Appl. No.: 16/611,975

(22) PCT Filed: May 9, 2018

(86) PCT No.: PCT/US2018/031879
§ 371 (c)(1),
(2) Date: Nov. 8, 2019

(87) PCT Pub. No.: WO2018/208971
PCT Pub. Date: Nov. 15, 2018

(65) Prior Publication Data
US 2021/0060148 A1 Mar. 4, 2021

Related U.S. Application Data

(60) Provisional application No. 62/504,132, filed on May 10, 2017.

(51) Int. Cl.
*A61K 39/00* (2006.01)
*A61P 35/00* (2006.01)
*A61K 35/545* (2015.01)
*C07K 14/535* (2006.01)
*C12N 5/0735* (2010.01)
*C12N 5/074* (2010.01)

(52) U.S. Cl.
CPC .... *A61K 39/001139* (2018.08); *A61K 35/545* (2013.01); *A61P 35/00* (2018.01); *C07K 14/535* (2013.01); *C12N 5/0606* (2013.01); *C12N 5/0696* (2013.01); *C12N 2510/00* (2013.01)

(58) Field of Classification Search
CPC ... C07K 14/535; A61K 35/545; C12N 5/0606
See application file for complete search history.

(56) References Cited

U.S. PATENT DOCUMENTS

| 2004/0071687 A1 | 4/2004 | Rafii et al. |
| 2009/0226508 A1 | 9/2009 | Eaton et al. |
| 2013/0323197 A1 | 12/2013 | Ratajczak et al. |

FOREIGN PATENT DOCUMENTS

WO   WO 2016/149358   9/2016

OTHER PUBLICATIONS

Chaput et al., "The potential of exosomes in immunotherapy", Expert Opin Biol Ther 5:737-747 (2005).
Colombo, et al., "Biogenesis, secretion, and intercellular interactions of exosomes and other extracellular vesicles," Annu Rev Cell Dev Biol 30:255-289 (2014).
Dong, W. et al., "Administration of embryonic stem cells generates effective antitumor immunity in mice with minor and heavy tumor load," Cancer Immunol Immun 59:1697-1705 (2010).
Gehrmann, et al., "Harnessing the exosome-induced immune response for cancer immunotherapy," Semin Cancer Biol 28:58-67 (2014).
ISA/US, The International Search Report and Written Opinion of the International Searching Authority for International Application No. PCT/US2018/031879 dated Aug. 3, 2018, 14 pgs.
Kooreman, et al., "Autologous iPSC-Based Vaccines Elicit Antitumor Responses In Vivo," Cell Stem Cell 22:501-513.(2018).
Kunigelis, K. E., et al., "The Dichotomy of Tumor Exosomes (TEX) in Cancer Immunity: Is It All in the ConTEXt?," Vaccines 3:1019-1051 (2015).
Li, Y., Zeng, et al., "Vaccination with Human Pluripotent Stem Cells Generates a Broad Spectrum of Immunological and Clinical Responses Against Colon Cancer," Stem Cells 27:3103-3111 (2009).
Mignot, G., et al., "Prospects for exosomes in immunotherapy of cancer," J Cell Mol Med 10:376-388 (2006).
Raposo, et al., "B lymphocytes secrete antigen-presenting vesicles," J Exp Med 183:1161-1172 (1996).
Shoemaker & Forsthuber, "Targeting "Retired Antigens" for Cancer Immunoprevention," Cancer Prev Res (Phila) 10:607-608 (2017).
Stonehill, E. H., et al., "Retrogenetic Expression—Reappearance of Embryonal Antigens in Cancer Cells," Nature 228:370-372 (1970).
Viaud, et al., "Dendritic cell-derived exosomes promote natural killer cell activation and 25 proliferation: a role for NKG2D ligands and IL-15R-alpha," PLoS One 4:e4942 (2009).
WIPO, International Preliminary Report on Patentability for International Application No. PCT/US2018/031879 dated Nov. 21, 2019, 7 pgs.

(Continued)

*Primary Examiner* — Elly-Gerald Stoica
(74) *Attorney, Agent, or Firm* — Jenkins, Wilson, Taylor & Hunt, P.A.

(57) ABSTRACT

Provided are compositions, optionally pharmaceutical compositions, that include a plurality of exosomes generated from stem cells, optionally ESCs and/or iPSCs, that have been modified to express a granulocyte-macrophage colony stimulating factor (GM-CSF) polypeptide, optionally a human GM-CSF polypeptide. Also provided are methods for employing the presently disclosed compositions for preventing and/or inhibiting tumor growth in subjects in need thereof, for preventing and/or inhibiting metastases in subject in need thereof, for inducing anti-tumor immune responses in subjects, and uses of the presently disclosed compositions for prevention and/or treatment of tumors and/or cancers and for the preparation of medicaments for treatment of tumors and/or cancers.

15 Claims, 17 Drawing Sheets

Specification includes a Sequence Listing.

(56) References Cited

OTHER PUBLICATIONS

Yaddanapudi, K. et al., "Vaccination with Embryonic Stem Cells Protects against Lung Cancer: Is a Broad-Spectrum Prophylactic Vaccine against Cancer Possible?," Plos One 7 (2012).
Zitvogel, et al., "Eradication of established murine tumors using a novel cell-free vaccine: dendritic cell-derived exosomes," Nat Med 4:594-600 (1998).
Yang et al., Systematic Identification of Factors for Provirus Silencing in Embryonic Stem Cells. Cell 163:230-245. (2015).

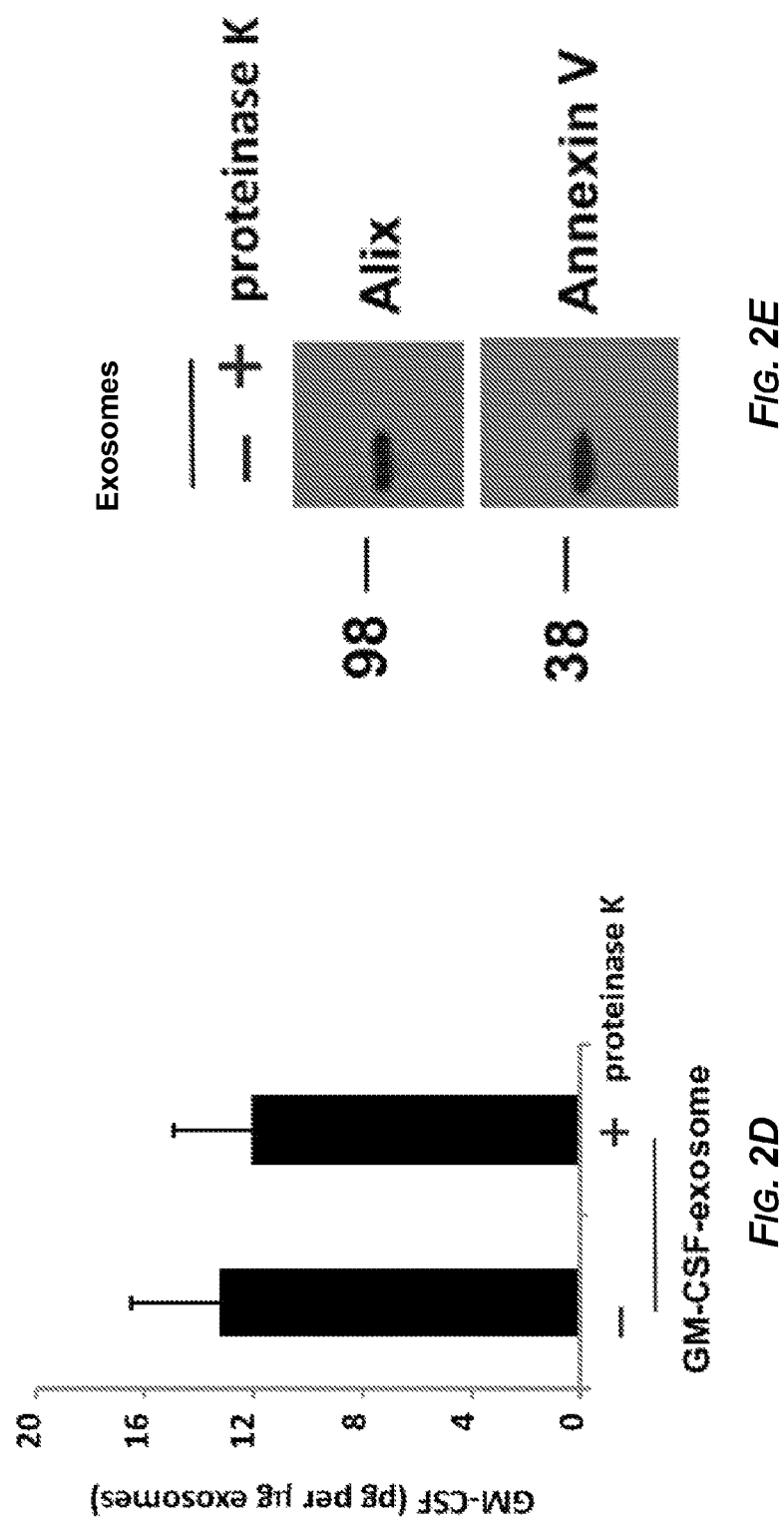

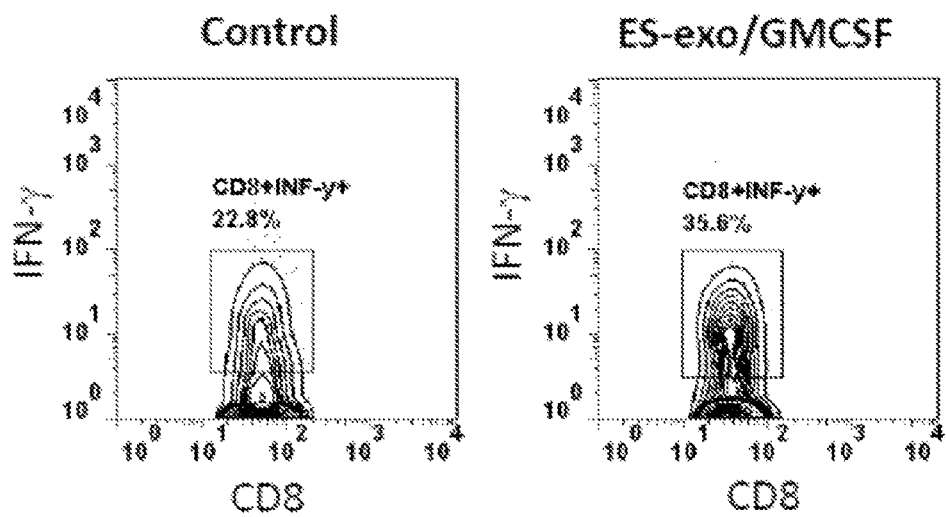
FIG. 4D
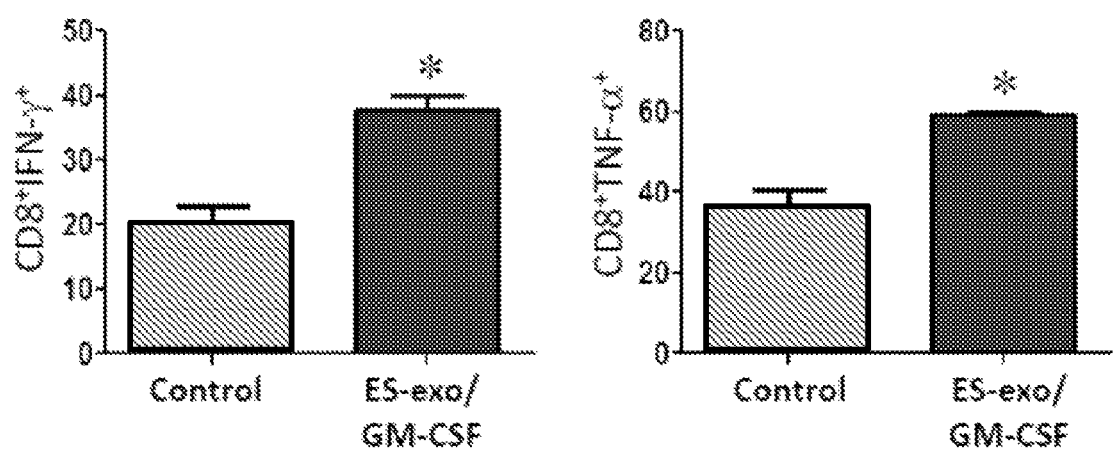
FIG. 4E
FIG. 4F

SEQUENCE LISTING

<160> NUMBER OF SEQ ID NOS: 4

<210> SEQ ID NO 1
<211> LENGTH: 800
<212> TYPE: DNA
<213> ORGANISM: Homo sapiens
<220> FEATURE:
<221> NAME/KEY: CDS
<222> LOCATION: (33)..(467)

<400> SEQUENCE: 1

```
acacagagag aaaggctaaa gttctctgga gg atg tgg ctg cag agc ctg ctg          53
                                    Met Trp Leu Gln Ser Leu Leu
                                    1               5 ctc ttg ggc act gtg gcc tgc agc atc tct gca ccc gcc cgc tcg ccc         101
Leu Leu Gly Thr Val Ala Cys Ser Ile Ser Ala Pro Ala Arg Ser Pro
        10                  15                  20 agc ccc agc acg cag ccc tgg gag cat gtg aat gcc atc cag gag gcc         149
Ser Pro Ser Thr Gln Pro Trp Glu His Val Asn Ala Ile Gln Glu Ala
    25                  30                  35 cgg cgt ctc ctg aac ctg agt aga gac act gct gct gag atg aat gaa         197
Arg Arg Leu Leu Asn Leu Ser Arg Asp Thr Ala Ala Glu Met Asn Glu
40                  45                  50                  55 aca gta gaa gtc atc tca gaa atg ttt gac ctc cag gag ccg acc tgc         245
Thr Val Glu Val Ile Ser Glu Met Phe Asp Leu Gln Glu Pro Thr Cys
                60                  65                  70 cta cag acc cgc ctg gag ctg tac aag cag ggc ctg cgg ggc agc ctc         293
Leu Gln Thr Arg Leu Glu Leu Tyr Lys Gln Gly Leu Arg Gly Ser Leu
            75                  80                  85 acc aag ctc aag ggc ccc ttg acc atg atg gcc agc cac tac aag cag         341
Thr Lys Leu Lys Gly Pro Leu Thr Met Met Ala Ser His Tyr Lys Gln
        90                  95                 100 cac tgc cct cca acc ccg gaa act tcc tgt gca acc cag att atc acc         389
His Cys Pro Pro Thr Pro Glu Thr Ser Cys Ala Thr Gln Ile Ile Thr
    105                 110                 115 ttt gaa agt ttc aaa gag aac ctg aag gac ttt ctg ctt gtc atc ccc         437
Phe Glu Ser Phe Lys Glu Asn Leu Lys Asp Phe Leu Leu Val Ile Pro
120                 125                 130                 135 ttt gac tgc tgg gag cca gtc cag gag tga gaccggccag atgaggctgg           487
Phe Asp Cys Trp Glu Pro Val Gln Glu
                140 ccaagccggg gagctgctct ctcatgaaac aagagctaga aactcaggat ggtcatcttg       547 gagggaccaa gggtgtggcc acagccatgg tgggagtggc ctggacctgc cctgggccac       607 actgaccctg atacaggcat ggcagaagaa tgggaatatt ttatactgac agaaatcagt       667 aatatttata tatttatatt tttaaaatat ttatttattt atttatttaa gttcatattc       727 catatttatt caagatgttt taccgtaata attattatta aaaatatgct tctacttgaa       787 aaaaaaaaaa aaa                                                          800
```

<210> SEQ ID NO 2
<211> LENGTH: 144
<212> TYPE: PRT
<213> ORGANISM: Homo sapiens

<400> SEQUENCE: 2

```
Met Trp Leu Gln Ser Leu Leu Leu Leu Gly Thr Val Ala Cys Ser Ile
1               5                   10                  15

Ser Ala Pro Ala Arg Ser Pro Ser Pro Ser Thr Gln Pro Trp Glu His
            20                  25                  30
```

```
Val Asn Ala Ile Gln Glu Ala Arg Arg Leu Leu Asn Leu Ser Arg Asp
         35                  40                  45

Thr Ala Ala Glu Met Asn Glu Thr Val Glu Val Ile Ser Glu Met Phe
 50                  55                  60

Asp Leu Gln Glu Pro Thr Cys Leu Gln Thr Arg Leu Glu Leu Tyr Lys
 65                  70                  75                  80

Gln Gly Leu Arg Gly Ser Leu Thr Lys Leu Lys Gly Pro Leu Thr Met
                 85                  90                  95

Met Ala Ser His Tyr Lys Gln His Cys Pro Pro Thr Pro Glu Thr Ser
                100                 105                 110

Cys Ala Thr Gln Ile Ile Thr Phe Glu Ser Phe Lys Glu Asn Leu Lys
            115                 120                 125

Asp Phe Leu Leu Val Ile Pro Phe Asp Cys Trp Glu Pro Val Gln Glu
130                 135                 140
```

```
<210> SEQ ID NO 3
<211> LENGTH: 1033
<212> TYPE: DNA
<213> ORGANISM: Mus musculus
<220> FEATURE:
<221> NAME/KEY: CDS
<222> LOCATION: (290)..(715)

<400> SEQUENCE: 3
ggtcagactg cccaggcagg gtgggaaagg cctttaaagc agcccgcagg tgggctgcca      60
gttcttggaa gggcttatta atgaaaaccc cccaagcctg acaacctggg ggaaggctca     120
ctggccccat gtatagctga taagggccag gagattccac aactcaggta gttccccgc      180 cccctggag ttctgtggtc accattaatc atttcctcta actgtgtata agagctct        240 tttgcagtga gccagtact cagagagaaa ggctaaggtc ctgaggagg atg tgg ctg      298
                                                    Met Trp Leu
                                                     1 cag aat tta ctt ttc ctg ggc att gtg gtc tac agc ctc tca gca ccc      346
Gln Asn Leu Leu Phe Leu Gly Ile Val Val Tyr Ser Leu Ser Ala Pro
      5                  10                  15 acc cgc tca ccc atc act gtc acc cgg cct tgg aag cat gta gag gcc      394
Thr Arg Ser Pro Ile Thr Val Thr Arg Pro Trp Lys His Val Glu Ala
 20                  25                  30                  35 atc aaa gaa gcc ctg aac ctc ctg gat gac atg cct gtc acg ttg aat      442
Ile Lys Glu Ala Leu Asn Leu Leu Asp Asp Met Pro Val Thr Leu Asn
                 40                  45                  50 gaa gag gta gaa gtc gtc tct aac gag ttc tcc ttc aag aag cta aca      490
Glu Glu Val Glu Val Val Ser Asn Glu Phe Ser Phe Lys Lys Leu Thr
             55                  60                  65 tgt gtg cag acc cgc ctg aag ata ttc gag cag ggt cta cgg ggc aat      538
Cys Val Gln Thr Arg Leu Lys Ile Phe Glu Gln Gly Leu Arg Gly Asn
         70                  75                  80 ttc acc aaa ctc aag ggc gcc ttg aac atg aca gcc agc tac tac cag      586
Phe Thr Lys Leu Lys Gly Ala Leu Asn Met Thr Ala Ser Tyr Tyr Gln
     85                  90                  95 aca tac tgc ccc cca act ccg gaa acg gac tgt gaa aca caa gtt acc      634
Thr Tyr Cys Pro Pro Thr Pro Glu Thr Asp Cys Glu Thr Gln Val Thr
100                 105                 110                 115 acc tat gcg gat ttc ata gac agc ctt aaa acc ttt ctg act gat atc      682
Thr Tyr Ala Asp Phe Ile Asp Ser Leu Lys Thr Phe Leu Thr Asp Ile
                120                 125                 130 ccc ttt gaa tgc aaa aaa cca ggc caa aaa tga ggaagcccag gccagctctg    735
Pro Phe Glu Cys Lys Lys Pro Gly Gln Lys
            135                 140
```

-continued

```
aatccagctt ctcagactgc tgcttttgtg cctgcgtaat gagccaggaa cttggaattt      795
ctgccttaaa gggaccaaga gatgtggcac agccacagtt ggaaggcagt atagccctct      855
gaaaacgctg actcagcttg gacagcggaa gacaaacgag agatattttc tactgatagg      915
gaccattata tttatttata tatttatatt tttaaaatat ttatttattt atttatttat      975
ttttgcaact ctatttattg agaatgtctt accagaataa taaattatta aaactttt      1033
```

<210> SEQ ID NO 4
<211> LENGTH: 141
<212> TYPE: PRT
<213> ORGANISM: Mus musculus

<400> SEQUENCE: 4

```
Met Trp Leu Gln Asn Leu Leu Phe Leu Gly Ile Val Val Tyr Ser Leu
1               5                   10                  15

Ser Ala Pro Thr Arg Ser Pro Ile Thr Val Thr Arg Pro Trp Lys His
            20                  25                  30

Val Glu Ala Ile Lys Glu Ala Leu Asn Leu Leu Asp Asp Met Pro Val
        35                  40                  45

Thr Leu Asn Glu Glu Val Glu Val Val Ser Asn Glu Phe Ser Phe Lys
    50                  55                  60

Lys Leu Thr Cys Val Gln Thr Arg Leu Lys Ile Phe Glu Gln Gly Leu
65                  70                  75                  80

Arg Gly Asn Phe Thr Lys Leu Lys Gly Ala Leu Asn Met Thr Ala Ser
                85                  90                  95

Tyr Tyr Gln Thr Tyr Cys Pro Pro Thr Pro Glu Thr Asp Cys Glu Thr
            100                 105                 110

Gln Val Thr Thr Tyr Ala Asp Phe Ile Asp Ser Leu Lys Thr Phe Leu
        115                 120                 125

Thr Asp Ile Pro Phe Glu Cys Lys Lys Pro Gly Gln Lys
    130                 135                 140
```

METHOD OF INHIBITING LUNG OR BREAST CANCER GROWTH WITH ENGINEERED EMBRYONIC STEM-CELL DERIVED EXOSOMES COMPOSITIONS

CROSS-REFERENCE TO RELATED APPLICATION

This application claims the benefit of U.S. Provisional Patent Application Ser. No. 62/504,132, filed May 10, 2017, the disclosure of which is incorporated herein by reference in its entirety.

GRANT STATEMENT

This invention was made with government support under Grant Nos. CA198249, CA106599, CA175003, GM106396, and AA018016 awarded by the National Institutes of Health. The government has certain rights in the invention

TECHNICAL FIELD

The presently disclosed subject matter relates to compositions comprising embryonic cell-derived exosomes/microvesicles that are engineered to produce GM-CSF. Also provided are methods for using the same as an anti-tumor vaccine.

BACKGROUND

A century has passed since Schöne reported experiments indicating that vaccination of animals with fetal material might prevent the outgrowth of tumors (Schone, 1906). Although this did not provoke an immediate flurry of research into this phenomenon, numerous publications did appear in the mid-1960's to 1970's on this topic reporting some successful results.

Although not completely understood in the early days of such research, any successful results might have been due to the similarities between embryonic/fetal and tumor antigens (the so-called carcinoembryonic or oncofetal antigens; reviewed in Brewer et al., 2009). Research activity in this area withered after the mid-1970s (apparently due to lack of funding), but recent reports indicate that such vaccination might hold promise for the prevention of cancers (Li et al., 2009; Dong et al., 2010; Yaddanapudi et al., 2012).

SUMMARY

This summary lists several embodiments of the presently disclosed subject matter, and in many cases lists variations and permutations of these embodiments. This summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently disclosed subject matter, whether listed in this summary or not. To avoid excessive repetition, this Summary does not list or suggest all possible combinations of such features.

In some embodiments, the presently disclosed subject matter provides compositions, optionally pharmaceutical compositions, comprising a plurality of exosomes generated from stem cells, in some embodiments embryonic stem cells (ESCs), in some embodiments induced pluripotent stem cells (iPSCs), and in some embodiments a combination thereof, that have been modified to express a granulocyte-macrophage colony stimulating factor (GM-CSF) polypeptide. In some embodiments, the stem cells are ESCs and in some embodiments the stem cells are induced pluripotent stem cells (iPSCs). In some embodiments, the stem cells are mammalian stem cells, which in some embodiments are human stem cells and in some embodiments are murine stem cells. In some embodiments, the GM-CSF polypeptide is a mammalian GM-CSF polypeptide, optionally a human GM-CSF polypeptide or a murine GM-CSF polypeptide. In some embodiments, the human GM-CSF polypeptide comprises an amino acid sequence as set forth in SEQ ID NO: 2 and/or is a functional fragment thereof and/or is at least 95% identical to SEQ ID NO: 2, optionally 95% identical to the full 144 amino acid length of SEQ ID NO: 2. In some embodiments, the murine GM-CSF polypeptide comprises an amino acid sequence as set forth in SEQ ID NO: 4 and/or is a functional fragment thereof and/or is at least 95% identical to SEQ ID NO: 4, optionally 95% identical to the full 141 amino acid length of SEQ ID NO: 4.

The presently disclosed subject matter also provides in some embodiments pharmaceutical compositions comprising compositions as disclosed herein and one or more a pharmaceutically acceptable carriers and/or excipients. In some embodiments, the pharmaceutically acceptable carriers and/or excipients are pharmaceutically acceptable for use in humans. In some embodiments, the pharmaceutical compositions further comprise an adjuvant and/or is administered in conjunction with an adjuvant.

The presently disclosed subject matter also provides in some embodiments methods for preventing and/or inhibiting tumor growth in subjects. In some embodiments, the methods comprising administering to a subject a pharmaceutical composition as disclosed herein in an amount and via a route of administration sufficient to prevent and/or inhibit tumor growth in the subject.

The presently disclosed subject matter also provides in some embodiments methods for preventing and/or inhibiting metastases in subjects in need thereof. In some embodiments, the methods comprising administering to a subject a pharmaceutical composition as disclosed herein in an amount and via a route of administration sufficient to prevent and/or inhibit metastases in the subject.

In some embodiments of the presently disclosed methods, the administering is subsequent to resection of a primary tumor from the subject.

In some embodiments of the presently disclosed methods, the subject is a human.

In some embodiments, the presently disclosed methods further comprise treating the subject with at least one additional anti-cancer therapy, optionally wherein the at least one additional anti-cancer therapy is selected from the group consisting of radiotherapy, chemotherapy, immunotherapy, surgery, and combinations thereof. In some embodiments, the at least one additional anti-cancer therapy comprises an immune checkpoint inhibitor. In some embodiments of the presently disclosed methods, the administering step is repeated at least once. In some embodiments of the presently disclosed methods, the at least one additional anti-cancer therapy is provided to the subject at a time prior to, concurrent with, subsequent to, or combinations thereof, the administering step.

The presently disclosed subject matter also provide in some embodiments uses of compositions comprising a plurality of exosomes generated from stem cells that have been modified to express a granulocyte-macrophage colony stimulating factor (GM-CSF) polypeptide, for the prevention and/or treatment of cancer and/or for the preparation of a medicament for the treatment of cancer. In some embodiments, the stem cells are embryonic stem cells (ESCs), induced pluripotent stem cells (iPSCs), or a combination thereof. In some embodiments, the ESCs and/or the iPSCs are mammalian ESCs and/or iPSCs. In some embodiments, the mammalian ESCs and/or iPSCs are human ESCs and/or iPSCs. In some embodiments, the GM-CSF polypeptide is a mammalian GM-CSF polypeptide, optionally a human GM-CSF polypeptide or a murine GM-CSF polypeptide.

In some embodiments, the presently disclosed subject matter provides methods for inducing anti-tumor immune responses in subjects. In some embodiments, the methods comprise administering to a subject a composition comprising one or more pharmaceutically acceptable carriers and/or excipients and a plurality of exosomes generated from stem cells that have been modified to express a granulocyte-macrophage colony stimulating factor (GM-CSF) polypeptide. In some embodiments, the stem cells are embryonic stem cells (ESCs), induced pluripotent stem cells (iPSCs), or a combination thereof. In some embodiments, the ESCs and/or the iPSCs are mammalian ESCs and/or iPSCs. In some embodiments, the mammalian ESCs and/or iPSCs are human ESCs and/or iPSCs. In some embodiments, the GM-CSF polypeptide is a mammalian GM-CSF polypeptide, optionally a human GM-CSF polypeptide or a murine GM-CSF polypeptide. In some embodiments, the anti-tumor immune response is sufficient to prevent occurrence of a tumor in the subject; delay occurrence of a tumor in the subject; reduce a rate at which a tumor develops in the subject; prevent recurrence of a tumor in the subject; suppress growth of a tumor in a subject; or any combination thereof. In some embodiments, the anti-tumor immune response comprises a cytotoxic T cell response against an antigen present in and/or on a cell of the tumor. In some embodiments, the subject is a human. In some embodiments, the cytotoxic T cell response is mediated by $CD8^+$ T cells.

Thus, it is an object of the presently disclosed subject matter to provide compositions and methods for inducing anti-tumor immune responses in subjects using exosomes generated from stem cells that have been modified to express a GM-CSF polypeptide.

An object of the presently disclosed subject matter having been stated hereinabove, and which is achieved in whole or in part by the presently disclosed subject matter, other objects will become evident as the description proceeds when taken in connection with the accompanying Figures as best described herein below.

BRIEF DESCRIPTION OF THE FIGURES

FIG. 1A is a schematic diagram of an expression vector (pEF1α-GM-CSF-Ires-GFP) with the EF1-α promoter ($P_{EF1\alpha}$) operably linked to a GM-CSF coding sequence (GM-CSF) and driving GM-CSF expression. The expression vector also includes an Internal Ribosome Entry Site (Ires) inserted downstream of the GM-CSF coding sequence and upstream of a Green Fluorescent Protein coding sequence (GFP), which allowed for expression of GFP protein. FIG. 1B is a bar graph that shows expression of GM-CSF in ES-D3 cells by transfection as measured by ELISA. The GM-CSF concentrations in the medium of the indicated cells is measured in ng/ml. The data are shown as mean one standard deviation of three independent experiments. FIG. 1C is a series of FACS scatterplots demonstrating maintenance of pluripotency of ES-D3 cells as shown by continued high expression of SSEA-1 and Oct-3/4 and low expression of SSEA-4 in parental cells (negative control with no vector; top panel), cells transfected with vector pEF1α-Ires-GFP (negative control vector that did not encode GM-CSF; middle panel), and cells transfected with the pEF1α-GM-CSF-Ires-GFP vector (bottom panel). The data shown are of three independent experiments.

FIGS. 2A-2E depict various characterizations of exosomes isolated from ESD3 cells. In FIG. 2A, exosomes were isolated from ES-D3 cells transfected with the plasmid expressing GM-CSF (right panel) or its empty vector (left panel). Transmission electron microscopy (TEM) imaging of the ESC-derived exosomes. Arrow heads indicate individual exosomes, Scale bar: 100 nm. FIG. 2B depicts Western blot analysis of the levels of the indicated exosomal markers (CD81, Alix, and Annexin V), endoplasmic reticulum (ER) markers (protein disulfide-isomerase (PDI) and calnexin), or a cytosolic marker (glyceraldehyde phosphate dehydrogenase; GAPDH) that were expressed in either in whole cell extracts or in the exosomes. FIG. 2C is a bar graph of concentration of GM-CSF in isolated exosomes measured using ELISA. The data are shown as mean±one standard deviation of three independent experiments. FIG. 2D is a bar graph of concentration of GM-CSF in exosomes from ESCs expressing GM-CSF treated with proteinase K, and GM-CSF levels evaluated using ELISA. The data are shown as mean one standard deviation of three independent experiments. FIG. 2E depicts Western blot analysis of the levels of exosome markers Alix and Annexin V in the ES-exosomes treated with or without proteinase K. The positions of 98 kiloDalton (kDa) and 38 kDa molecular weight markers are indicated to the left of the panel.

FIG. 3A outlines a representative scheme of immunization. Male C57BL/6 mice were immunized twice (days 0 and 7) with vehicle only (HBSS control), or with exosomes isolated from ES-D3 cells expressing the empty vector (ES-exo), or with exosomes isolated from ES-D3 cells over-expressing GM-CSF (ES-exo/GM-CSF) in the right flank prior to s.c. challenge with LLC cells on day 14. FIG. 3B is a graph showing the percentage of tumor-free mice at various times post-tumor challenge. C57BL/6 mice (20 mice/group) were immunized twice (days 0 and 7) with HBSS (control; open circles), or with exosomes isolated from ES-D3 cells expressing the empty vector (ES-exo; X), or with exosomes isolated from ES-D3 cells over-expressing GM-CSF (ES-exo/GM-CSF; black solid circles) in the right flank prior to s.c. challenge with LLC on day 14. Tumor growth was monitored daily in all animals until sacrifice due to tumors exceeding 5% of body weight. The ES-exo/GM-CSF vaccinated tumor free mice remained so for up to 4 months later with no overt signs of distress or autoimmunity. Results are representative of three independent experiments. ***, p<0.0001; relative to control group; log-rank test. FIG. 3C is a plot of tumor volume versus days post-tumor challenge in the same mice as in FIG. 3B. Tumor growth was measured by calipers every second or third day and tumor volumes were plotted as indicated. The data represent the average tumor volumes of 20 mice/control group and 8 mice/ES-exo/GM-CSF group and are representative of three independent experiments. Error bars represent mean±SEM. Solid squares: Vehicle Control. Solid circles: exosomes isolated from ES-D3 cells expressing the empty vector (Exosome alone). Open circles: exosomes isolated from ES-D3 cells over-expressing GM-CSF (Exosome+GMCSF).

FIGS. 4A-4F show the results of experiments demonstrating that ESC-derived exosome vaccination induced Th1-mediated cytokine responses in splenic and intra-tumoral $CD8^+$ T cells. In FIGS. 4A-4C, C57BL/6 mice (4 mice/group) were immunized twice (days 0 and 7) with HBSS (control), or with exosomes isolated from ES-D3 cells over-expressing GM-CSF (ES-exo/GM-CSF) in the right flank. Ten days after the boost, mice were euthanized and spleens were removed. Splenocytes from vaccinated and control mice were co-cultured with LLC lysate (50 μg/ml) for an additional 4 days. Effectors were harvested and stimulated for 4 hours with PMA (50 ng/ml) and ionomycin (500 ng/ml) in the presence of Brefeldin A (1 μL/ml). After restimulation, effectors were harvested, Fc receptors were blocked, and stained for surface expression of CD4, CD8 and intracellular expression of cytokines and analyzed by flow cytometry. FIG. 4A is a pair of dot plots showing IFN-γ expression in $CD8^+$ cells in splenocyte cultures obtained from control (left panel) and ES-exo/GM-CSF vaccinated (right panel) mice. Numbers in quadrants represent the percentages of each subpopulation. FIGS. 4B and 4C are bar graphs showing percentages of $CD8^+IFN-γ^+$ cells (FIG. 4B) and $CD8^+TNF-α^+$ cells (FIG. 4C) cells in splenocyte cultures derived from control and ES-exo/GM-CSF vaccinated mice. Results are expressed as percentages of total cells. In FIGS. 4D-4F, ESC-derived exosome vaccination induced Th1-mediated cytokine response in intra-tumoral $CD8^+$ T cells. C57BL/6 mice (4 mice/group) were immunized twice (days 0 and 7) with HBSS (control), or with exosomes isolated from ES-D3 cells over-expressing GM-CSF (ES-exo/GM-CSF) in the right flank prior to s.c. challenge with LLC on day 14. Mice were euthanized 15-18 days after tumor challenge and tumors were removed and enzymatically digested. Tumor-infiltrating cells from vaccinated and control mice were stimulated for 6 hours with PMA (50 ng/ml) and ionomycin (500 ng/ml) in the presence of Brefeldin A (1 μL/ml). After restimulation, tumor cells were harvested, Fc receptors were blocked, stained for surface expression of CD45, CD3, and CD8, and intracellular expression of IFN-γ and analyzed by flow cytometry. FIG. 4D is a pair of dot plots showing IFN-γ expression in $CD45^+CD3^+CD8^+$ cells in tumor-infiltrating cells obtained from control (left panel) and vaccinated (right panel) mice. Numbers in quadrants represent the percentages of each subpopulation. FIGS. 4E and 4F are bar graphs showing percentages of $CD45^+CD3^+CD8^+IFN-γ^+$ cells (FIG. 4E) and $CD45^+CD3^+CD8^+TNF-α^+$ cells (FIG. 4F) in tumors derived from control and ES-exo/GM-CSF exosome vaccinated mice. Results are expressed as percentages of total $CD45^+$ cells. Tumor-infiltrating cells were isolated from 4 mice per group. Error bars represent mean±SEM. *, p<0.05 relative to control group; t test.

FIG. 5A is a pair of dot plots showing percentages of splenic $CD4^+CD25^+Foxp3^+$ T regulatory cells in control (left panel) and ES-exo/GM-CSF vaccinated (right panel) mice. Numbers in quadrants represent the percentages of each subpopulation. FIG. 5B is a bar graph showing percentages of $CD4^+CD25^+Foxp3^+$ T regulatory cells ($T_{reg}$) in splenocytes obtained from control and ES-exo/GM-CSF vaccinated mice. Results are expressed as percentages of total cells. FIG. 5C shows the ratio of $CD8^+Foxp3^-$ to $CD4^+CD25^+Foxp3^+$ $T_{reg}$ cells was calculated and compared in splenocytes obtained from control and ES-exo/GM-CSF vaccinated mice. FIG. 5D is a bar graph showing percentages of $CD4^+$ T, $CD8^+$ T, and B cells in splenocytes obtained from control and ES-exo/GM-CSF vaccinated mice. Results are expressed as percentages of total cells. Three independent analyses were performed with cells from 4 mice per group; data from one representative assay is shown. Error bars represent mean±SEM. FIG. 5E is a bar graph showing percentages of $CD11b^+GR1^+$ myeloid-derived suppressor cells (MDSCs) in splenocytes obtained from control and ES-exo/GM-CSF vaccinated mice. Results are expressed as percentages of total cells. FIG. 5F is a bar graph showing percentages of $CD11b^+GR1^-CD11c^+$ dendritic cells in splenocytes obtained from control and ES-exo/GM-CSF vaccinated mice. Results are expressed as percentages of total cells. *: p<0.05 relative to control group; t test.

FIG. 6A is a series of dot plots showing the percentages of $CD3^+CD4^+Foxp3^+T_{regs}$ in $CD45^+$ tumor-infiltrating cells obtained from control (top panel) and GM-CSF exosome vaccinated (bottom panel) mice. In each panel of FIG. 6A, the left dot plot shows $CD45^+CD3^+$ T cells and the right dot plot shows $CD3^+CD4^+Foxp3^+$ $T_{regs}$. Numbers in quadrants represent the percentages of each subpopulation. FIG. 6B is a bar graph showing the percentages of $CD3^+CD4^+Foxp3^+$ $T_{regs}$ sub-populations in $CD45^+$ tumor infiltrating cells from control and ES-exo/GM-CSF vaccinated mice. Results are expressed as percentages of total $CD45^+$ cells. Tumor-infiltrating cells were isolated from 4 mice per group. FIG. 6C is a graph showing the ratio of $CD8^+$ $Foxp3^-$ to $CD8^-Foxp3^+$ cells in 1 of 2 representative experiments with 4 mice/group. FIG. 6D is a bar graph showing the percentages of $CD25^+CD8^+$ in $CD45^+$ tumor-infiltrating cells obtained from control and ES-exo/GM-CSF vaccinated mice. Results are expressed as percentages of total cells. The data represent results from 2 independent experiments with 4 mice/group. FIG. 6E is a bar graph showing the percentages of $CD11b^+Gr-1^+$ MDSCs sub-populations in $CD45^+$ tumor infiltrating cells. Results are expressed as percentages of total $CD45^+$ cells. Tumor-infiltrating cells were isolated from 4 mice per group. FIGS. 6F and 6G are bar graphs showing the percentages of $CD11b^+Gr-1^-CD11c^+$ dendritic cells (FIG. 6F) and percentages of $CD11b^+Gr-1^-F4-80^+$ macrophages (FIG. 6G) in $CD45^+$ tumor-infiltrating cells obtained from control and ES-exo/GM-CSF vaccinated mice. Numbers in quadrants represent the percentages of each subpopulation. Error bars represent mean±SEM. *: p<0.05; relative to control group; t test.

BRIEF DESCRIPTION OF THE SEQUENCE LISTING

Figure 1A:
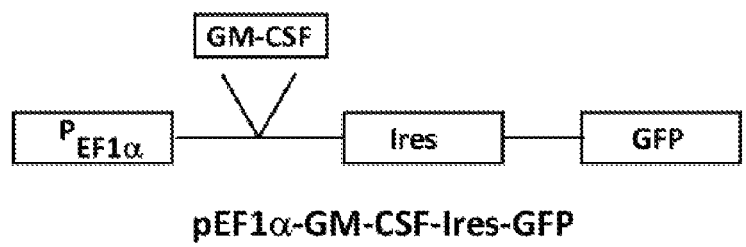
FIGS. 1A-1C show the results of experiments demonstrating that murine embryonic stem cells expressing GM-CSF maintained their pluripotency.

SEQ ID NO: 1 is a nucleotide sequence of a human CG-CSF gene product disclosed as Accession Number NM_000758.3 of the GENBANK® biosequence database. SEQ ID NO: 1 encodes an amino acid sequence disclosed as Accession Number NP_000749.2 of the GENBANK® biosequence database, which is presented as SEQ ID NO: 2.

SEQ ID NO: 3 is an amino acid sequence of a murine CG-CSF gene product disclosed as Accession Number NP_034099.2 of the GENBANK® biosequence database. SEQ ID NO: 3 is encoded by the nucleotide sequence disclosed as Accession Number NM_009969.4 of the GENBANK® biosequence database, which is presented as SEQ ID NO: 4.

DETAILED DESCRIPTION

The presently disclosed subject matter relates, in general, to compositions and methods for prevention of and/or treatment of a tumor and/or a cancer. More particularly, the presently disclosed subject matter relates to administering prophylactic and/or therapeutic compositions comprising exosomes generated and/or derived from stem cells to a subject in need thereof. Also provided are methods for employing the presently disclosed compositions for preventing and/or inhibiting tumor growth in subjects in need thereof, for preventing and/or inhibiting metastases in subject in need thereof, for inducing anti-tumor immune responses in subjects, and uses of the presently disclosed compositions for prevention and/or treatment of tumors and/or cancers and for the preparation of medicaments for treatment of tumors and/or cancers.

I. DEFINITIONS

All technical and scientific terms used herein, unless otherwise defined below, are intended to have the same meaning as commonly understood by one of ordinary skill in the art. References to techniques employed herein are intended to refer to the techniques as commonly understood in the art, including variations on those techniques or substitutions of equivalent techniques that would be apparent to one of skill in the art. While the following terms are believed to be well understood by one of ordinary skill in the art, the following definitions are set forth to facilitate explanation of the presently disclosed subject matter.

While the following terms are believed to be well understood by one of ordinary skill in the art, the following definitions are set forth to facilitate explanation of the presently disclosed subject matter.

Unless otherwise indicated, all numbers expressing quantities of ingredients, reaction conditions, and so forth used in the instant disclosure and claims are to be understood as being modified in all instances by the term "about". Accordingly, unless indicated to the contrary, the numerical parameters set forth in instant disclosure and claims are approximations that can vary depending upon the desired properties sought to be obtained by the presently disclosed subject matter.

Following long-standing patent law tradition, the terms "a", "an", and "the" are meant to refer to one or more as used herein, including in the claims. For example, the phrase "a cell" can refer to one or more cells. Also as used herein, the term "another" can refer to at least a second or more.

The term "about", as used herein when referring to a measurable value such as an amount of weight, time, dose (e.g., a number of cells), etc., is meant to encompass variations of in some embodiments ±20%, in some embodiments ±10%, in some embodiments, ±5%, in some embodiments ±1%, and in some embodiments ±0.1% from the specified amount, as such variations are appropriate to perform the disclosed methods.

The use of the term "or" in the instant disclosure and claims is used to mean "and/or" unless explicitly indicated to refer to alternatives only or the alternatives are mutually exclusive.

As used herein, the words "comprising" (and any form of comprising, such as "comprise" and "comprises"), "having" (and any form of having, such as "have" and "has"), "including" (and any form of including, such as "includes" and "include"), or "containing" (and any form of containing, such as "contains" and "contain") are inclusive or open-ended and do not exclude additional, unrecited elements or method steps.

As used herein, the term "adjuvant" refers to a substance that elicits an enhanced immune response when used in combination with a composition of the presently disclosed subject matter. Exemplary adjuvants include, but are not limited to montanide ISA-51, QS-21, tetanus helper peptides, GM-CSF, cyclophosamide, *Bacillus* Calmette-Guerin (BCG), *Corynbacterium parvum*, levamisole, azimezone, isoprinisone, dinitrochlorobenezene (DNCB), keyhole limpet hemocyanins (KLH), incomplete Freunds adjuvant, complete Freunds adjuvant, mineral gels, aluminum hydroxide (Alum), lysolecithin, pluronic polyols, polyanions, peptides, oil emulsions, dinitrophenol, and diphtheria toxin (DT).

As used herein, the term "exosome" refers to nanovesicles released from a variety of different cells. These small vesicles can be derived from large multivesicular endosomes and secreted into the extracellular milieu. The precise mechanisms of exosome release/shedding remain unclear. They appear to form by invagination and budding from the limiting membrane of late endosomes, resulting in vesicles that contain cytosol and that expose the extracellular domain of membrane-bound cellular proteins on their surface. As used herein, an exosome is said to be "generated from a stem cell" if the exosome is released from a stem cell (e.g., an ESC, an iPSC cell, etc.).

As used herein, the phrases "GM-CSF gene product" and "GM-CSF polypeptide" refer in some embodiments to a full length granulocyte-macrophage colony stimulating factor (also referred to as colony stimulating factor 2) polypeptide as well as to fragments thereof that have at least a fraction of an immunomodulatory activity of the full length polypeptide. Coding sequences for GM-CSFs from several species are publicly available in the GENBANK® database including, but not limited to GENBANK® Accession Nos. NM_000758 (*Homo sapiens*); XM_527005 (*Pan troglodytes*); NM_001003245 (*Canis familiaris*); NM_214118 (*Sus scrofa*); NM_009969 (*Mus musculus*); and NM_053852 (*Rattus norvegicus*). These coding sequences encode GM-CSF polypeptides having the amino acid sequences as set forth in GENBANK® Accession Nos. NP_000749 (*Homo sapiens*); XP_527005 (*Pan troglodytes*); NP_001003245 (*Canis familiaris*); NP_999283 (*Sus* scrofa); NP_034099 (*Mus musculus*); and NP_446304 (*Rattus norvegicus*). As used herein, a "GM-CSF gene product" or "GM-CSF polypeptide" can be from any species such as but not limited to a mammal, including but not limited to a human or a mouse.

As used herein, the terms "nucleic acid" and "nucleic acid molecule" mean any of deoxyribonucleic acid (DNA), ribonucleic acid (RNA), oligonucleotides, fragments generated by the polymerase chain reaction (PCR), and fragments generated by any of ligation, scission, endonuclease action, and exonuclease action. Nucleic acids can be composed of monomers that are naturally occurring nucleotides (such as deoxyribonucleotides and ribonucleotides), or analogs of naturally occurring nucleotides (e.g., α-enantiomeric forms of naturally-occurring nucleotides), or a combination of both. Nucleic acids can be either single stranded or double stranded.

The terms "identical" or percent "identity" in the context of two or more nucleotide or polypeptide sequences, refer to two or more sequences or subsequences that are the same or have a specified percentage of amino acid residues or nucleotides that are the same, when compared and aligned for maximum correspondence, as measured using one of the sequence comparison algorithms disclosed herein or by visual inspection. For sequence comparison, typically one sequence acts as a reference sequence to which test sequences are compared. When using a sequence comparison algorithm, test and reference sequences are entered into a computer program, subsequence coordinates are designated if necessary, and sequence algorithm program parameters are selected. The sequence comparison algorithm then calculates the percent sequence identity for the designated test sequence(s) relative to the reference sequence, based on the selected program parameters. In some embodiments, a percent identity is calculated over the full length of one or both of the two sequences being compared.

Optimal alignment of sequences for comparison can be conducted, e.g., by the local homology algorithm of Smith & Waterman, 1981; by the homology alignment algorithm of Needleman & Wunsch, 1970; by the search for similarity method of Pearson & Lipman, 1988; by computerized implementations of these algorithms (e.g., GAP, BESTFIT, FASTA, and TFASTA), or by visual inspection. See generally, Ausubel et al., 1992.

An exemplary algorithm for determining percent sequence identity and sequence similarity is the BLAST algorithm, which is described in Altschul et al., 1990. Software for performing BLAST analyses is publicly available through the website of the United States National Center for Biotechnology Information (NCBI). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold. These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when the cumulative alignment score falls off by the quantity X from its maximum achieved value, the cumulative score goes to zero or below due to the accumulation of one or more negative-scoring residue alignments, or the end of either sequence is reached. The BLAST algorithm parameters W, T, and X determine the sensitivity and speed of the alignment. The BLASTN program (for nucleotide sequences) uses as defaults a wordlength W=11, an expectation E=10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix. See Henikoff & Henikoff, 1989.

In addition to calculating percent sequence identity, the BLAST algorithm also performs a statistical analysis of the similarity between two sequences. See e.g., Karlin & Altschul, 1993. One measure of similarity provided by the BLAST algorithm is the smallest sum probability (P(N)), which provides an indication of the probability by which a match between two nucleotide or amino acid sequences would occur by chance. For example, a test nucleic acid sequence is considered similar to a reference sequence if the smallest sum probability in a comparison of the test nucleic acid sequence to the reference nucleic acid sequence is in some embodiments less than about 0.1, in some embodiments less than about 0.01, and in some embodiments less than about 0.001.

As used herein, the term "polypeptide" means any polymer comprising any of the 20 protein amino acids, or amino acid analogs, regardless of its size or function. Although "protein" is often used in reference to relatively large polypeptides, and "peptide" is often used in reference to small polypeptides, usage of these terms in the art overlaps and varies. The term "polypeptide" as used herein refers to peptides, polypeptides and proteins, unless otherwise noted. As used herein, the terms "protein", "polypeptide" and "peptide" are used interchangeably. The term "polypeptide" encompasses proteins of all functions, including enzymes.

As used herein, "significance" or "significant" relates to a statistical analysis of the probability that there is a non-random association between two or more occurrences. To determine whether or not a relationship is "significant" or has "significance", statistical manipulations of the data can be performed to calculate a probability, expressed as a "p-value". Those p-values that fall below a user-defined cutoff point are regarded as significant. In some embodiments, a p-value less than or equal to 0.10, in some embodiments less than or equal to 0.05, in some embodiments less than or equal to 0.01, in some embodiments less than or equal to 0.005, and in some embodiments less than or equal to 0.001, are regarded as significant.

The term "subject" as used herein refers to a member of any invertebrate or vertebrate species. The methods of the presently disclosed subject matter are particularly useful for warm-blooded vertebrates. Thus, the presently disclosed subject matter concerns mammals and birds. Provided in some embodiments is the treatment and/or prophylaxis of tumors in mammals such as humans, as well as those mammals of importance due to being endangered (such as Siberian tigers), of economic importance (animals raised on farms for consumption by humans) and/or social importance (animals kept as pets or in zoos) to humans, for instance, carnivores other than humans (such as cats and dogs), swine (pigs, hogs, and wild boars), ruminants (such as cattle, oxen, sheep, giraffes, deer, goats, bison, and camels), and horses. Also provided is the use of the disclosed methods and compositions on birds, including those kinds of birds that are endangered, kept in zoos, as well as fowl, and more particularly domesticated fowl, e.g., poultry, such as turkeys, chickens, ducks, geese, guinea fowl, and the like, as they are also of economic importance to humans. Thus, provided is the use of the disclosed methods and compositions in livestock, including but not limited to domesticated swine (pigs and hogs), ruminants, horses, poultry, and the like. In some embodiments, the stem cells from which the exosomes are generated and/or derived and the GM-CSF gene product the stem cells are modified to express are from the same species as the subject to which the exosomes are to be administered.

As used herein, the phrases "treatment effective amount", "therapeutically effective amount", "treatment amount", and "effective amount" are used interchangeably and refer to an amount of a composition (e.g., a composition comprising exosomes generate and/or derived from a stem cell and one or more pharmaceutically acceptable carriers and/or excipients) sufficient to produce a measurable response (e.g., a biologically or clinically relevant response in a subject being treated). For example, actual dosage levels of exosomes in the compositions of the presently disclosed subject matter can be varied so as to administer a sufficient number of exosomes to achieve the desired immune response for a particular subject. The selected dosage level will depend upon several factors including, but not limited to the route of administration, combination with other drugs or treatments, the severity of the condition being treated, and the condition and prior medical history of the subject being treated.

Additionally, in the context of the prophylactic methods disclosed herein, a phrases "treatment effective amount", "therapeutically effective amount", "treatment amount", and "effective amount" refer to an amount that elicits an immune response sufficient to provide a prophylactic benefit to the subject. In some embodiments, a prophylactic benefit is provided by inducing an immune response to an antigen and/or epitope present in the composition sufficient to prevent the initial occurrence and/or growth of a tumor and/or a cancer, delay the occurrence and/or growth of a tumor and/or a cancer in the subject, reduce a rate at which a tumor develops in the subject; or combinations thereof.

The terms "cancer" and "tumor" are used interchangeably herein and can refer to both primary and metastasized solid tumors and carcinomas of any tissue in a subject, including but not limited to breast; colon; rectum; lung; oropharynx; hypopharynx; esophagus; stomach; pancreas; liver; gallbladder; bile ducts; small intestine; urinary tract including kidney, bladder, and urothelium; female genital tract including cervix, uterus, ovaries (e.g., choriocarcinoma and gestational trophoblastic disease); male genital tract including prostate, seminal vesicles, testes and germ cell tumors; endocrine glands including thyroid, adrenal, and pituitary; skin (e.g., hemangiomas and melanomas), bone or soft tissues; blood vessels (e.g., Kaposi's sarcoma); brain, nerves, eyes, and meninges (e.g., astrocytomas, gliomas, glioblastomas, retinoblastomas, neuromas, neuroblastomas, Schwannomas and meningiomas). The terms "cancer and "tumor" also encompass solid tumors arising from hematopoietic malignancies such as leukemias, including chloromas, plasmacytomas, plaques and tumors of mycosis fungoides and cutaneous T-cell lymphoma/leukemia, and lymphomas including both Hodgkin's and non-Hodgkin's lymphomas. As used herein, the terms "cancer and "tumor" are also intended to refer to multicellular tumors as well as individual neoplastic or pre-neoplastic cells. In some embodiments, a tumor is an adenoma and/or an adenocarcinoma, in some embodiments a lung adenoma and/or adenocarcinoma.

II. COMPOSITIONS

II.A. Generally

Previous attempts to produce a prophylactic vaccine employed irradiated allogeneic murine embryonic stem cells (ESCs) and murine fibroblasts expressing GM-CSF as an immune stimulant (Yaddanapudi et al., 2012). However, such an approach has at least two disadvantages in terms of application to humans: (1) the use of live ESCs—although putatively allogeneic—raises the hazard of the generation of embryomas/teratomas; and (2) using murine fibroblasts to generate GM-CSF is needlessly complicated.

Disclosed herein are improvements with respect to the safety and utility of a vaccine that employs exosomes generated and/or derived from stem cells, including but not limited to ESCs and iPSCs, which have been engineered to generate GM-CSF in amounts similar to those produced by the afore-mentioned fibroblasts. Using these modified stem cells, stem cell-derived exosomes were generated and purified, thereby producing a self-contained, relatively stable exosome-based vaccine while at the same time obviating the need for administration of intact, live ESCs).

Exosomes are cell-derived nanovesicles that are typically 50-100 nm (Colombo et al., 2014) that have recently gained renewed interest as they unveil immense potential for cancer therapy (Gehrmann et al., 2014). In vitro and in vivo studies suggest that exosomes communicate via an acellular mode, leading to intercellular transfer of molecules (Thery et al., 2002). Importantly, exosomes seem to also transfer nucleic acids such as mRNA and microRNA and thus, represent a new paradigm of genetic exchange between cells (Valadi et al., 2007). Recent studies indicate that exosomes can operate as potential immunotherapeutic agents, with promising results in pre-clinical studies of cancer immunotherapy (Gehrmann et al., 2014).

As disclosed herein, in a prophylactic setting, vaccination of mice with ESC-exosomes expressing GM-CSF (ES-exo/GM-CSF) is very effective in preventing implantable lung tumors with no detectable toxicity or signs of autoimmunity. Importantly, anti-tumor efficacy of the ES-exo/GM-CSF combination vaccine is associated with robust $CD8^+$ T effector responses and infiltration of $CD8^+$ T cells into the tumor, leading to increased intratumoral $CD8^+$ T effector/T regulatory cell ratio in the tumors. Collectively, the present disclosure provides strong support for employing the presently disclosed exosome-based vaccination strategies for the prevention and/or treatment of tumors and/or cancers.

The compositions of the presently disclosed subject matter comprise a plurality of exosomes generated from stem cells, optionally embryonic stem cells (ESCs) and/or induced pluripotent stem cells (iPSCs), that have been modified to express a granulocyte-macrophage colony stimulating factor (GM-CSF) polypeptide, optionally a mammalian GM-CSF polypeptide, which in some embodiments is a human GM-CSF polypeptide or a murine GM-CSF polypeptide. Standard molecular biological techniques can be employed for modifying stem cells including but not limited to ESCs and/or iPSCs to express exogenous gene products. See e.g., Sambrook & Russell (2001) *Molecular Cloning: A Laboratory Manual* (3rd ed.) Cold Spring Harbor Laboratory Press, Cold Spring Harbor, N.Y., United States of America.

An exemplary stem cell is thus an embryonic stem cell (ESC). As used herein, the phrase "embryonic stem cell" (ESC) refers to a pluripotent or totipotent stem cell that is in some embodiments isolated and/or derived from (in some embodiments, a progeny cell thereof) the inner cell mass of a blastocyst and grown in culture under conditions that maintain their status as pluripotent or totipotent stem cells. ESCs can also be derived and/or isolated from primordial germ cells (PGCs) located in the mesenteric or genital ridges of days 8.5-12.5 post coitum mouse embryos (Matsui et al., 1991; Resnick et al., 1992; U.S. Pat. Nos. 5,453,357; 5,690,926; 7,153,684), although these cells have also been referred to as embryonic germ cells (EGCs). Both ESCs and EGCs are (at least) pluripotent and demonstrate germline genetic transmission in the mouse. Human ESCs and EGCs have also been established (see e.g., U.S. Pat. Nos. 6,245,566; 6,331,406; 6,875,607)

ESCs are undifferentiated, pluripotent cells typically derived in vitro from early embryos (Evans et al., 1981; Martin, 1981). ESCs can maintain an undifferentiated state through serial passages using culturing techniques that are known in the art (see e.g., Robertson et al., 1987; Williams et al., 1988; Nagy et al., 1990; Nagy et al., 2003). In some embodiments, ESCs are cultured on a fibroblast feeder layer and/or in the presence of Leukemia Inhibitory Factor (LIF) to maintain an undifferentiated state.

The cells of a feeder layer are typically mitotically inactivated with mitomycin C or gamma irradiation. An exemplary fibroblast cell that can be used to produce a feeder layer is the STO cell (ATCC® No. CRL-1503™, American Type Culture Collection (ATCC®), Manassas, Va., United States of America). Additionally, some feeder cells are available that have been modified to express LIF and/or a neomycin resistance gene (neo), the latter of which can be employed to grow ESCs and ESC derivatives that have been transformed with an expression vector encoding a neomycin phosphotransferase (neo) coding sequence. In some embodiments, if a LIF-producing feeder cell is employed, the use of additional LIF in the ESC propagation medium can be avoided. STO derivatives are available that have been modified to express both LIF and neo, such as the SNL76/7 fibroblast line described in McMahon & Bradley, 1990. Other STO cell lines that have been modified to express both LIF and neo.

Alternatively or in addition, ESCs can be grown on a monolayer of murine embryonic fibroblasts (MEFs) that have been prepared as described in, for example, Loo & Costman, 1998. MEFs can also be prepared from a mouse embryo that has been genetically altered to express a selectable marker (see e.g., Tucker et al., 1997, describing a mouse that expresses resistance genes to G418, 6-thioguanine, puromycin, and hygromycin), which can aid in the propagation of ESCs and ESC derivatives that have been transformed with recombinant vectors.

In some embodiments including, for example, when the ESCs are intended for use in producing a vaccine for administration into humans, the presence of a feeder layer comprising cells from a species other than humans is disfavored. U.S. Pat. No. 6,800,480 to Bodnar et al. and U.S. Patent Application Publication No. 20060030042 of Brivanlou et al. disclose methods and materials for the growth of stem cells in a feeder-free culture. Thus, in some embodiments, the ESCs are maintained in culture in the absence of a feeder layer and maintained in an undifferentiated state by the addition of exogenous growth factors including, but not limited to LIF. It is understood that any cell culture technique including, but not limited to feeder-free culture and serum-free culture, can be employed with respect to the stem cells of the presently disclosed subject matter.

For example, when the ESCs are intended for use in producing a vaccine for administration into humans, the growth of the ESCs in animal serum (e.g., bovine serum) is disfavored. U.S. Patent Application Publication No. 20050266553 to Pebay & Pera discloses a method and materials for the growth of stem cells in a serum-free culture. Thus, in some embodiments, the ESCs are maintained in a culture medium absent animal serum and maintained in an undifferentiated state. Culture conditions that can be employed for growing and maintaining human ESCs are known (see e.g., U.S. Pat. No. 9,279,103).

Stem cells (e.g., ESCs, iPSCs, or combinations thereof) from any species can be employed in the compositions and methods disclosed herein. The stem cells can but need not be from the same species as the subject into which the compositions of the presently disclosed subject matter are administered. Thus, in some embodiments, allogeneic stem cells (i.e., from the same species as the subject) are employed, but in some embodiments xenogeneic stem cells (i.e., from a different species than the subject) are employed. Murine ESC lines are commercially available (e.g., from the American Type Culture Collection, Manassas, Va., United States of America), and ESCs from other species including humans and other primates (see e.g., U.S. Pat. Nos. 5,843,780; 6,200,806; 6,875,607; and 6,921,632; and Thomson et al., 1995, 1996), birds (see e.g., U.S. Pat. Nos. 5,340,740; 5,656,479; and 5,830,510), and pigs (Li et al., 2004) have also been produced. In some embodiments, the compositions disclosed herein comprise human stem cells.

It is understood that a function of the stem cells, derivatives thereof, and/or fractions thereof disclosed herein is to provide one or more antigens that are shared between the stem cells and a cancer cell to a subject to which they are administered. Thus, the stem cell's status as being pluripotent is not determinative of the cell's usefulness in the presently disclosed methods and compositions. Indeed, other cells and cell types can be employed in the disclosed methods and compositions. For example, such cells and cell types include, but are not limited to early primitive ectoderm-like (EPL) cells as described in PCT International Patent Application Publication WO 99/53021; in vivo or in vitro derived inner cell mast/epiblast; in vivo or in vitro derived primitive ectoderm; primordial germ cells (PGCs), including embryonic germ (EG) cells derived therefrom; teratocarcinoma cells (EC cells), and cells derived by dedifferentiation or by nuclear transfer.

With respect to EG cells, these cells are ES-like cells that can be generated from primordial germ cells (PGCs) from several different species including, but not limited to mice (see U.S. Pat. Nos. 5,453,357; 5,670,372; 5,690,926; all to Hogan), pigs (see U.S. Pat. No. 6,271,436 to Piedrahita & Bazer), bovines (U.S. Pat. No. 6,011,197 to Strelchenko et al.), avians (U.S. Pat. No. 6,333,192), and humans (see U.S. Pat. Nos. 6,090,622; 6,245,566; and 6,331,406; all to Gearhart & Shamblott). See also Shamblott et al., 1998. These cells are also intended to be encompassed by the phrase "stem cells" as that phrase is used herein.

A second exemplary stem cell is an "induced pluripotent stem cell" (iPSC; iPS cell). As used herein, the phrase "induced pluripotent stem cell" (iPSC; iPS cell) refers to cells having properties similar to those of ESCs, and more particularly, undifferentiated cells having pluripotency and growth ability that are derived from adult cells or other non-stem cells that have been manipulated in vitro to are "dedifferentiate" (i.e., that acquire a degree of pluripotency that is greater than the cell prior to the manipulation). iPSCs were originally generated by transfection of adult cells with particular gene products (Oct4, Sox2, cMyc, and Klf4), which together generated ESC-like colonies from fibroblasts (Takahashi & Yamanaka, 2006; see also U.S. Pat. Nos. 8,058,065; 8,278,104). In recent years, mouse and human iPSCs have been successively established. Exemplary methods for preparing induced pluripotent stem cells by using a nuclear reprogramming factor is explained in, for example, PCT International Patent Application Publication Nos. WO 2005/080598 and WO 2007/069666 (see also U.S. Pat. Nos. 7,964,401 and 8,048,999). Subsequently, it has been revealed that iPS cells can also be prepared using 3 of the above factors (excluding the c-Myc gene; see Nakagawa et al., 2008; Takahashi et al., 2007). Another group has prepared human iPS cells using Nanog and Lin28 instead of Klf4 and c-Myc (see PCT International Patent Application Publication No. WO 2008/118820; U.S. Pat. No. 8,440,461; and Yu et al., 2007).

In some embodiments, the stem cell(s) and thus the exosomes generated and/or derived therefrom, and the GM-CSF polypeptide are all mammalian, and in some embodiments are all from the same species. For example, if a composition is to be administered to a human, the stem cells are in some embodiments human ESCs, in some embodiments human iPSCs, and in some embodiments are a mixture thereof, and thus the exosomes to be administered are human exosomes. In some embodiments, the stem cells are in some embodiments human ESCs and/or iPSCs and the GM-CSF polypeptide the stem cells are modified to express is a human GM-CSF polypeptide, a functional fragment thereof, and/or is a polypeptide having an amino acid sequence that is at least 95% identical to a human GM-CSF polypeptide sequence such as but not limited to SEQ ID NO: 2.

II.B. Formulations

In some embodiments, the compositions of the presently disclosed subject matter are pharmaceutical compositions. Thus, the compositions of the presently disclosed subject matter comprise in some embodiments a pharmaceutically acceptable carrier. Any suitable formulation can be used to prepare the disclosed compositions for administration to a subject. In some embodiments, the pharmaceutically acceptable carrier is pharmaceutically acceptable for use in a human.

For example, suitable formulations can include aqueous and non-aqueous sterile injection solutions which can contain anti-oxidants, buffers, bacteriostats, bactericidal antibiotics and solutes which render the formulation isotonic with the bodily fluids of the intended recipient; and aqueous and non-aqueous sterile suspensions which can include suspending agents and thickening agents. The formulations can be presented in unit-dose or multi-dose containers, for example sealed ampoules and vials, and can be stored in a frozen or freeze-dried (lyophilized) condition requiring only the addition of sterile liquid carrier, for example water for injections, immediately prior to use. Some exemplary ingredients are SDS, in some embodiments in the range of 0.1 to 10 mg/ml, in some embodiments about 2.0 mg/ml; and/or mannitol or another sugar, in some embodiments in the range of 10 to 100 mg/ml and in some embodiments about 30 mg/ml; and/or phosphate-buffered saline (PBS).

It should be understood that in addition to the ingredients particularly mentioned above, the formulations of the presently disclosed subject matter can include other agents conventional in the art having regard to the type of formulation in question. Of the possible formulations, sterile pyrogen-free aqueous and non-aqueous solutions can be used.

The methods and compositions of the presently disclosed subject matter can be used with additional biologically active entities including, but not limited to, cytokines (e.g., IFN-α, IFN-γ, IL-2, IL-4, IL-6, IL-12, TNF, GM-CSF), adjuvants (e.g., complete or incomplete Freund's adjuvant and other art-recognized immunomodulatory adjuvants), anti-tolerance compositions (e.g., antibodies and other compositions directed against regulatory T-cells ($T_{regs}$) including, but not limited to anti-CTLA4 antibodies and ONTAK® (Denileukin diftitox, a composition comprising the diphtheria toxin fragments A and B fused to sequences for interleukin-2 (IL-2) that is available from Ligand Pharmaceuticals, Inc., San Diego, Calif., United States of America)), combinations thereof, and/or other immunomodulatory compositions. In accordance with this aspect of the presently disclosed subject matter, the disclosed compositions can be administered in combination therapy with one or more of these biologically active entities.

In some embodiments, the additional biologically active entity is an immune checkpoint inhibitor. Any immune checkpoint inhibitor can be employed in conjunction with the methods and compositions of the presently disclosed subject matter, including but not limited to PD-1 inhibitors (e.g., pembrolizumab, sold under the brand name KEYTRUDA® by Merck Sharp & Dohme Corp., Whitehouse Station, N.J., United States of America; and/or nivolumab, sold under the brand name OPDIVO® by Bristol-Myers Squibb Company, New York, N.Y., United States of America), PD-L1 inhibitors (e.g., atezolizumab, sold under the brand name TECENTRIQ® by Genentech USA, Inc., South San Francisco, Calif., United States of America; avelumab, sold under the brand name BAVENCIA® by EMD Serono, Inc., Rockland, Mass., United States of America; and/or durvalubab, sold under the brand name IMFINZI® by AstraZeneca, Gaithersburg, Md., United States of America), and drugs that target CTLA-4 such as ipilimumab (sold under the brand name YERVOY® by Bristol-Myers Squibb Company, New York, N.Y., United States of America).

In some embodiments, the composition comprises exosomes generated and/or derived from stem cells that have been modified to express a granulocyte-macrophage colony stimulating factor (GM-CSF) polypeptide or a functional fragment thereof. As used herein, the term "functional fragment" refers to a polypeptide comprising a subsequence of the amino acid sequence of a GM-CSF polypeptide, with the proviso that the polypeptide comprising the subsequence is characterized by having at least a partial immunomodulatory activity of that possessed by a naturally occurring GM-CSF polypeptide. In some embodiments, the immunomodulatory activity is an immunostimulatory activity, and the functional fragment has at least 10%, 20%, 25%, 30%, 40%, 50%, 60%, 70%, 75%, 80%, 90%, 95%, or 100% of the immunostimulatory activity of a wild type GM-CSF polypeptide from the same species as the subject to be treated and/or the in assay by which the activity is tested.

The GM-CSF polypeptide, or the functional fragment thereof, can be employed in any of many forms. In some embodiments, the GM-CSF that is employed is a recombinant GM-CSF polypeptide. The recombinant GM-CSF polypeptide can be produced by recombinant DNA techniques that are well known in the art (see e.g., Sambrook & Russell, 2001, for a discussion of recombinant polypeptide production). Depending on the species of the subject to which the composition is to be administered, a coding sequence encoding a GM-CSF polypeptide from the appropriate species can be transformed into a cell (e.g., a cell line for the same species) and the recombinant protein purified using standard techniques. Coding sequences for GM-CSFs from several species are publicly available in the GENBANK® database including, but not limited to GENBANK® Accession Nos. NM_000758 (*Homo sapiens*); XM_527005 (*Pan troglodytes*); NM_001003245 (*Canis familiaris*); NM_214118 (*Sus scrofa*); NM_009969 (*Mus musculus*); and XM_340799 (*Rattus norvegicus*). Each of these sequences is incorporated by reference in its entirety, including all annotations present in the corresponding entry that is accessible from the webpage of the National Center for Biotechnology Information (NCBI) of the United States of America, which also includes amino acid sequences encoded thereby.

II.C. Administration

A composition of the presently disclosed subject matter can be administered to a subject in need thereof in any manner that would be expected to generate an immune response in the subject to at least one antigen present within the composition. Suitable methods for administration of a composition of the presently disclosed subject matter include, but are not limited to, intravenous (i.v.), intraperitoneal (i.p.), subcutaneous (s.c.), subdermal (s.d.), intramuscular (i.m.), and/or intratumoral injection, and inhalation.

II.D. Doses

The presently disclosed subject matter methods comprise administering a therapeutically effective dose of a composition of the presently disclosed subject matter to a subject in need thereof. As defined hereinabove, an "effective amount" is an amount of the composition sufficient to produce a measurable response (e.g., a cytolytic and/or cytotoxic response in a subject being treated). It is understood, however, that the measurable response might not become manifest unless and until the subject develops a tumor or pre-tumor, thereby re-exposing the subject's immune system to an antigen and/or an epitope found on or in an exosome present in the composition. In some embodiments, the measurable response comprises an activity that inhibits or reduces a rate of tumor growth, or even substantially prevents tumor development and growth. As such, it is noted that the phrase "sufficient to prevent and/or inhibit tumor growth" encompasses any measurable degree to which tumor growth is prevented or inhibited, including a reduction in the rate at which a tumor grows, a complete inhibition of tumor growth, and a degree of inhibition that results in a complete or partial reduction in the size of a tumor.

Actual dosage levels of active ingredients in the compositions of the presently disclosed subject matter can be varied so as to administer an amount of the presently disclosed exosomes that is effective to achieve the desired response for a particular subject. The selected dosage level can depend upon the activity of the composition, the route of administration, combination with other drugs or treatments, the severity of the condition being treated, and the condition and prior medical history of the subject being treated. However, it is within the skill of the art to start doses of the compositions at levels lower than required to achieve the desired effect and to gradually increase the dosage until the desired effect is achieved. In some embodiments of the compositions of the presently disclosed subject matter, the exosomes are present in the composition in an amount ranging from about $1\times10^5$ to about $1\times10^6$ exosomes per dose. In some embodiments, the exosomes are present in the composition in an amount ranging from about $1\times10^6$ to about $1\times10^7$ exosomes per dose. In some embodiments, greater than $10^7$ exosomes per dose are present in the composition. It is recognized that this dosage level, which has been shown to be effective in a rodent model, can also be adjusted as necessary for administration to other subjects (including but not limited to subjects of other species) taking into consideration, for example, the size and/or blood volume of the subject. It is within the ability of the skilled artisan in the medical field to extrapolate dosages among different species and among different members of the same species by taking into account these and optionally other parameters.

After review of the disclosure herein of the presently disclosed subject matter, one of ordinary skill in the art can tailor the dosages to an individual subject, taking into account the particular formulation, method of administration to be used with the composition, and/or characteristics of the tumor itself, including but not limited to size, growth rate, and number. Further calculations of dose can consider patient height and weight, severity and stage of symptoms, and the presence of additional deleterious physical conditions. Such adjustments or variations, as well as evaluation of when and how to make such adjustments or variations, are known and/or would be apparent to those of ordinary skill in the art upon a review of the instant disclosure.

III. METHODS OF USE

III.A. Methods of Prophylaxis

The compositions and methods disclosed herein can be employed for both prophylaxis against as well as treatment for the development of tumor and/or cancer cells, including non-neoplastic and neoplastic cells.

Thus, in some embodiments the presently disclosed compositions are employed as prophylactic vaccines, and the presently disclosed subject matter provides methods for vaccinating a subject against occurrence of a tumor (i.e., the spontaneous development of a tumor arising from the subject's own cells) in a subject. In some embodiments, the methods comprise administering to a subject in need thereof a composition comprising a plurality of exosomes and one or more pharmaceutically acceptable carriers or excipients.

As used herein, the terms "prophylaxis" and grammatical variants thereof are to be interpreted broadly to encompass not only prevention of the initial occurrence of a tumor and/or a cancer, but also to encompass intermediate levels of prophylaxis including, but not limited to delaying the occurrence and/or re-occurrence of a tumor and/or a cancer in the subject, reducing a rate at which a tumor develops in the subject; and combinations thereof.

In some embodiments, the prophylactic treatments of the presently disclosed subject matter induce in the subject an anti-tumor and/or anti-cancer immune response. In some embodiments, the immune response is sufficient to (a) prevent occurrence of a tumor in the subject; (b) delay occurrence of a tumor in the subject; (c) reduce a rate at which a tumor develops in the subject; (d) prevent recurrence of a tumor in the subject; (e) suppress growth of a tumor in a subject; or (f) combinations thereof. In some embodiments, the immune response comprises a cytotoxic T cell response. In some embodiments, the subject is a human, and in some embodiments the cytotoxic T cell response is mediated by $CD8^+$ T cells.

Subjects in need of a prophylactic treatment include subjects that are more likely than the general population to develop a tumor or a cancer. In some embodiments, a human subject in need of prophylactic treatment includes a subject that has a genetic predisposition to developing a certain type of tumor and/or cancer. Genetic bases for disorders of abnormal cellular proliferation have been identified and include, but are not limited to genotypes associated with an increased risk of developing familial adenomatous polyposis (FAP; associated with certain alleles of the APC gene); breast cancer (BRCA1 and 2 genes); and colon cancer (DCC gene).

In some embodiments, a human subject in need of prophylactic treatment includes a subject that is predisposed to developing a certain type of tumor and/or cancer as a result of intentional or unintentional exposure to various environmental insults (e.g., cigarette smoking/lung cancer, asbestos exposure/mesothelioma). The methods and compositions disclosed herein can be employed prior to the appearance of any such tumor and/or cancer in an effort to "prime" the immune system of the subject so that the subject's immune system will develop a more robust response to the tumor or cancer, or to an earlier pre-neoplastic precursor cell of the tumor or cancer, than it would have in the absence of the prophylactic treatment.

The nature of the prophylactic treatment as a vaccine is such that the treatment is provided by administering to the subject in need thereof a pharmaceutical composition comprising a plurality of exosomes generated from stem cells, optionally embryonic stem cells (ESCs), induced pluripotent stem cells (iPSCs), or a combination thereof, which have been modified to express a granulocyte-macrophage colony stimulating factor (GM-CSF) polypeptide (e.g., a mammalian GM-CSF polypeptide) in an amount and via a route of administration sufficient to prevent or inhibit tumor growth and/or prevent and/or inhibit metastases in the subject. As used herein, the phrase "prevent and/or inhibit metastases" refers to any measurable extent to which metastases in a subject is prevented or inhibited as compared to the extent to which metastases in the subject would have occurred had the prophylactic treatment not been administered.

As is known in the art, the prophylactic treatment can comprise one administration, or in some embodiments, an initial administration followed by one or more subsequent administrations.

III.B. Methods of Treatment

The presently disclosed subject matter compositions and methods can also be employed as a part of a treatment regimen for subjects that already have a tumor and/or a cancer. Thus, the presently disclosed subject matter also provides methods for preventing the further development and/or proliferation of a tumor and/or a cancer including but not limited to preventing and/or inhibiting tumor growth.

In some embodiments, the methods disclosed herein comprise administering to a subject having a cancer or a tumor a pharmaceutical composition comprising a plurality of exosomes generated from stem cells, optionally embryonic stem cells (ESCs), induced pluripotent stem cells (iPSCs), or a combination thereof, which have been modified to express a granulocyte-macrophage colony stimulating factor (GM-CSF) polypeptide (e.g., a mammalian GM-CSF polypeptide) in an amount and via a route of administration sufficient to prevent and/or inhibit tumor growth in the subject.

The methods disclosed herein can be employed for treating any tumor and/or cancer in a subject, including but not limited to bladder carcinoma, breast carcinoma, cervical carcinoma, cholangiocarcinoma, colorectal carcinoma, gastric sarcoma, glioma, lung carcinoma, lymphoma, melanoma, multiple myeloma, osteosarcoma, ovarian carcinoma, pancreatic carcinoma, prostate carcinoma, stomach carcinoma, head tumors, neck tumors, and solid tumors. In some embodiments, the tumor comprises a lung carcinoma.

As is known to those of skill in oncology, combination treatments are frequently employed to treat neoplastic disease. Thus, the presently disclosed compositions and methods can be a part of a broader anti-cancer treatment (i.e., can constitute an adjuvant therapy in combination with other treatments). As such, in some embodiments the presently disclosed methods further comprise providing to the subject an additional anti-tumor therapy such as radiation, chemotherapy, surgical resection of the tumor, or combinations thereof. The additional anti-tumor therapy or combination therapies can be provided to the subject at a time prior to, concurrent with, or subsequent to administering the presently disclosed compositions, and the presently disclosed compositions can be administered at more than one of these time points.

III.C. Combined Prophylactic/Treatment Methods

In some embodiments, the methods and compositions disclosed herein can be employed for both prophylactic and treatment purposes. An example of a medical condition for which such a combination use would be appropriate would involve the administration to a subject of a composition as disclosed herein to prevent the outgrowth of minimal residual disease (MRD) after the cessation of other shorter term treatments (e.g., surgery, irradiation, and/or chemotherapy). As is known to the medical oncologist, MRD is a significant risk factor for relapse, but is very difficult to detect. Thus, the subject that has concluded his or her cancer treatment is frequently left in doubt as to whether the treatment can be considered a "cure" or just a temporary improvement.

Given that MRD can often not be detected, subjects with MRD are characterized by having no observable tumors and/or cancer. These subjects can then undergo an initial administration of the presently disclosed compositions (or in the case of subjects that have already been administered the presently disclosed compositions, one or more follow-on administrations) in an effort to stimulate the subject's immune system to produce an anti-tumor and/or anti-cancer immune response to address his or her MRD. Employing such a strategy would be expected to minimize the number of more aggressive treatments (e.g., radiation and or chemotherapy) that a subject might require and/or increase the length of time between such treatments.

In some embodiments, the compositions and methods of the presently disclosed subject matter are administered to a subject to induce an anti-tumor immune response. As used herein, the phrase "anti-tumor response" refers to any response in a subject that prevents or inhibits the establishment, maintenance, growth, and/or metastasis of a tumor cell or a cancer cell in a subject. In some embodiments, the compositions and methods of the presently disclosed subject matter induce an anti-tumor immune response that is sufficient to prevent occurrence of a tumor in the subject; delay occurrence of a tumor in the subject; reduce a rate at which a tumor develops in the subject; prevent recurrence of a tumor in the subject; and/or suppress growth of a tumor in a subject; or any combinations thereof.

IV. OTHER USES

In some embodiments, the presently disclosed subject matter also relates to uses of the compositions and pharmaceutical compositions comprising a plurality of exosomes generated from stem cells that have been modified to express a granulocyte-macrophage colony stimulating factor (GM- CSF) polypeptide as disclosed herein, for the prevention and/or treatment of cancer. In some embodiments, the presently disclosed subject matter relates to uses of the compositions and pharmaceutical compostions comprising a plurality of exosomes generated from stem cells that have been modified to express a granulocyte-macrophage colony stimulating factor (GM-CSF) polypeptide disclosed herein in the preparation of a medicament for the treatment of cancer.

EXAMPLES

The following Examples provide illustrative embodiments. In light of the present disclosure and the general level of skill in the art, those of skill will appreciate that the following Examples are intended to be exemplary only and that numerous changes, modifications, and alterations can be employed without departing from the scope of the presently disclosed subject matter.

Materials and Methods for the Examples

Reagents.

KNOCKOUT™ brand Dulbecco's Modified Eagle's Medium (DMEM), β-mercaptoethanol, non-essential amino acids, G418, and gelatin were purchased from Thermo Fisher (Waltham, Mass., United States of America). Proteinase K and polybrene were obtained from Sigma (St. Louis, Mo., United States of America). Leukemia inhibitory factor was obtained from EMD Millipore (Billerica, Mass., United States of America). Penicillin/streptomycin, L-glutamine and trypsin were obtained from Mediatech (Manassas, Va., United States of America), and fetal bovine serum was purchased from ATCC (Manassas, Va., United States of America). Antibodies (Abs) for western blot were anti-Alix mAb; anti-Annexin V mAb (Santa Cruz; Dallas, Tex., United States of America), anti-calnexin pAb; anti-protein disulfide isomerase (PDI) pAb (Enzo; Farmingdale, N.Y., United States of America), peroxidase-conjugated goat anti-rabbit IgG; peroxidase-conjugated goat anti-mouse IgG (Thermo Fisher).

Plasmids.

The transfection expression vector pEF1α-IRES-hrGFP was generated by removing FD3ER cDNA from the plasmid pEF1α-FD3ER-IRES-hrGFP acquired from Addgene (Cambridge, Mass., United States of America). Murine GM-CSF cDNA was cloned into pEF1α-IRES-hrGFP to generate pEF1α-GM-CSF-IRES-hrGFP. The plasmid identities were validated by sequencing.

Generation of Cell Lines.

Murine embryonic stem cell line ES-D3 was acquired from ATCC (CRL-11632; Manassas, Va., United States of America), independently verified to be pathogen-free. ES-D3 cells were cultured in DMEM supplemented with 15% fetal bovine serum, 50 U/ml penicillin, 50 µg/ml streptomycin, 0.1 mM non-essential amino acids, 2 mM L-glutamine, 0.1 mM β-mercaptoethanol, and 100 units/ml leukemia inhibitory factor (LIF). ES-D3 cells were cultured without a feeder layer in dishes pre-coated with 0.1% gelatin. ES-D3 cells stably overexpressing GM-CSF were generated by transfection. To generate GM-CSF ES-D3 cells with stably transfected GM-CSF, pEF1α-GM-CSF-IRES-hrGFP or the empty vector was transfected into ES-D3 cells along with the plasmid pBabe-neo using LIPOFECTAMINE 2000® transfection reagent (Thermo Fisher). Stably transfected cells were acquired by culturing the cells in medium containing 0.5 mg/ml G418, and GFP-positive ES-D3 cells were subsequently acquired by flow cytometry sorting (Beckman Coulter; Brea, Calif.). Lewis lung carcinoma (LLC) cells (originally derived from C57BL6 mice) were obtained from ATCC and cultured under standard conditions in DMEM supplemented with 15% ES Cell Qualified fetal bovine serum. All the cell lines were cultured in a 5% $CO_2$ humidified incubator at 37° C. Cell lines were not cultured for longer than 6-8 weeks and all of stocks came from thawed vials that were frozen at passage two after receipt from ATCC. LLC and ES-D3 cell lines were authenticated by ATCC cell bank using the Short Tandem Repeat (STR) profiling (see e.g., Nims et al., 2010).

Exosomes/Microvesicles.

ES-D3 cells ($5 \times 10^6$) were cultured in 15 cm tissue culture dishes with 15 ml medium for 72 hours. Medium was then collected and centrifuged at 5,000×g for 60 minutes at 4° C. The medium was then centrifuged again at 100,000×g for 90 minutes at 4° C. Following removal of the medium, the pellets were washed twice using PBS and resuspended in PBS and protein concentrations of exosomes were measured using BCA (bicinchoninic acid) assay (Thermo Fisher). To prepare samples for electron microscopy, exosomes were fixed by incubating with 2% paraformaldehyde for 2 hours. Fixed exosomes were loaded on Cu grids with carbon support film (Electron Microscopy Sciences; Hatfield, Pa., United States of America) and stained with UranyLess staining solution (Electron Microscopy Sciences). The electron microscopy images were acquired on a Hitachi HT7700 transmission electron microscope (Hitachi, Ltd., Tokyo, Japan) at the Kentucky Biomedical Research Infrastructure Network (KBRIN) of the University of Louisville (Louisville, Ky., United States of America). For proteinase K treatment, exosomes (2 mg/mL) were incubated with 0.3 mg/ml proteinase K at 37° C. for 30 minutes. The reactions were stopped by putting the samples on ice.

ELISA.

The concentrations of GM-CSF in the ES-D3 cell supernatants and isolated exosomes were determined by a murine GM-CSF ELISA kit (Thermo Fisher) following the manufacturer's protocol. Briefly, samples were added to an ELISA plate coated with capture antibody. Following incubation with detection antibody and Avidin-HRP, the absorbance at 450 nM was determined using a microplate reader (PowerWave XS, BioTek Instruments, Inc.; Winooski, Vt., United States of America).

Western Blot Analysis.

Samples were separated on a 4-12% Bis-Tris gel (Bio-Rad; Hercules, Calif.) and transferred on to PVDF membranes (Millipore EMD, now Millipore Sigma, Burlington, Mass., United States of America). The membranes were incubated with appropriate primary and secondary antibodies in blotting buffer (PBS with 0.2% Tween®-20 brand nonionic detergent) supplemented with 10% (w/v) non-fat dried skimmed milk (Bio-Rad). Proteins were detected using an enhanced chemiluminescence detection system (Thermo Fisher).

Evaluation of Pluripotency.

The pluripotency of ES-D3 cells was evaluated using a STEMFLOW™ Human and Mouse Pluripotent Stem Cell Analysis Kit (Beckon Dickinson; San Jose, Calif., United States of America) following the manufacturer's protocol. The expression levels of SSEA-1, Oct-3/4, and SSEA-4 were measured using flow cytometry (FACSCALIBUR™, Beckon Dickinson, Franklin Lakes, N.J., United States of America).

Proteomics Analysis.

Proteins in the exosomes isolated from ES-D3 cells were exacted using a buffer containing 50 mM Tris (pH 7.4), 150 mM NaCl, 1% NP-40 and 0.05% SDS at 4° C. Protein samples were sent to University of California at Davis Genome Center for mass spectrometry analysis. The data were analyzed using Scaffold Proteome software (Portland, Oreg., United States of America).

Animal Handling.

Mice were handled in accord with Association for Assessment and Accreditation of Laboratory Animal Care International (AAALAC) International guidelines. The experiments were approved by the Institutional Animal Care and Use Committee of the University of Louisville.

Vaccination and Tumor Challenge.

Male C57BL/6 mice (20-22 g body weight, 6-8 weeks of age) were obtained from The Jackson Laboratory (Bar Harbor, Me., United States of America) and housed under standard conditions. Mice were immunized twice (days 0 and 7) with vehicle only (Hank's Balanced Salt Solution; HBSS), control exosomes (exosomes isolated from ES-D3 cells expressing the empty vector) or GM-CSF exosomes (isolated from ES-D3 cells stably-expressing GM-CSF). Exosomes were injected subcutaneously (s.c.) into the right flank of mice. Exosomal protein was adjusted to be equivalent to that of the previously used whole ESC vaccine ($1\times10^6$ cells). On day 14, mice were challenged with $1\times10^5$ Lewis lung carcinoma (LLC; obtained from ATCC) injected s.c. into the left flank. Tumor growth was measured by calipers every second day and tumor volumes were plotted.

Flow Cytometric Analysis.

Single cell suspensions from spleen were stained with relevant antibodies (CD3, CD4, CD8, CD44, CD62L, CD69, CD25, CD43, CD11b, Ly6G, Ly6C) for 30 minutes after blocking with CD16/CD32 antibody (2.4G2; BD Biosciences, San Jose, Calif., United States of America) for 15 minutes at 4° C. After washing, cell surface and intracellular stained cells were analyzed on a FACSCALIBUR™ (Becton Dickinson, Franklin Lakes, N.J.) and results were analyzed with FlowJo software (TreeStar, Inc., Ashland, Oreg., United States of America).

Intracellular Cytokine Staining.

Spleens were isolated from different treatment groups 10 days after the last vaccination. Splenocytes were stimulated with LLC lysate (50 mg/ml) for 4 days. For TNF-α and IFN-γ production, cells (effectors) were harvested and incubated for 4 hours with PMA (50 ng/ml) and ionomycin (500 ng/ml) in the presence of GOLGIPLUG™ brand protein transport inhibitor (containing brefeldin A; BD PharMingen, San Jose, Calif., United States of America) at a dilution of 1 µl/ml. After restimulation, effectors were harvested, Fe receptors were blocked, and stained for surface expression of CD4, CD8 and intracellular expression of cytokines using a CYTOFIX/CYTOPERM™ brand fixation/permeabilization kit according to the manufacturer's instructions (BD Pharmingen) and analyzed by flow cytometry.

Analysis of Tumor-Infiltrating T Cells.

Vaccinated and control mice bearing LLC tumors were euthanized 18-21 days after tumor challenge. Solid tumors were dissected and chopped into small pieces before incubation with a mixture of enzymes dissolved in HBSS (400 U/ml collagenase type IV, 0.05 mg/ml collagenase type I, 0.025 mg/ml hyaluronidase, all from Sigma-Aldrich, St. Louis, Mo., United States of America; 0.01 mg/ml DNase I from Boehringer Mannheim, Ridgefield, Conn., United States of America) for 2 hours at 37° C. with occasional shaking. The resultant cells were washed and passed through a Ficoll gradient to eliminate dead cells. Tumor infiltrating lymphocytes (TILs) were then analyzed by flow cytometry for the expression of CD4, CD8, and CD25 markers. T regulatory cells ($T_{reg}$; Foxp3+) were analyzed using the anti-mouse Foxp3 staining kit (eBioscience). The same number of cells (based on side-scatter and forward-scatter analyses) was acquired in all samples. Anti-CD45 antibody was used to selectively exclude CD45− tumor cells from analysis. For intracellular IFN-γ analysis, TILs were stimulated with PMA and Ionomycin for 8 hours in the presence of Brefeldin A.

Statistical Analysis.

StatView version 5.0.1 software (Windows version; SAS Institute, Cary, N.C., United States of America) or GraphPad Prism 5.0 software (GraphPad Prisim Software, Inc., La Jolla, Calif., United States of America) were used for all statistical analyses. Comparisons between groups were done using Student's t test or one-way analysis of variance (ANOVA) where appropriate. Survival curves were analyzed using the log-rank test. Statistical significance was assumed at $p<0.05$.

Example 1

Stable Expression of GM-CSF in Pluripotent Murine Embryonic Cells

Figure 1B:
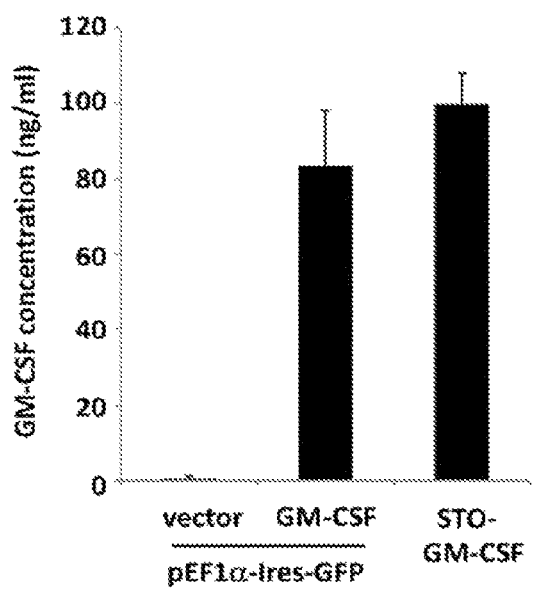
Figure 1C:
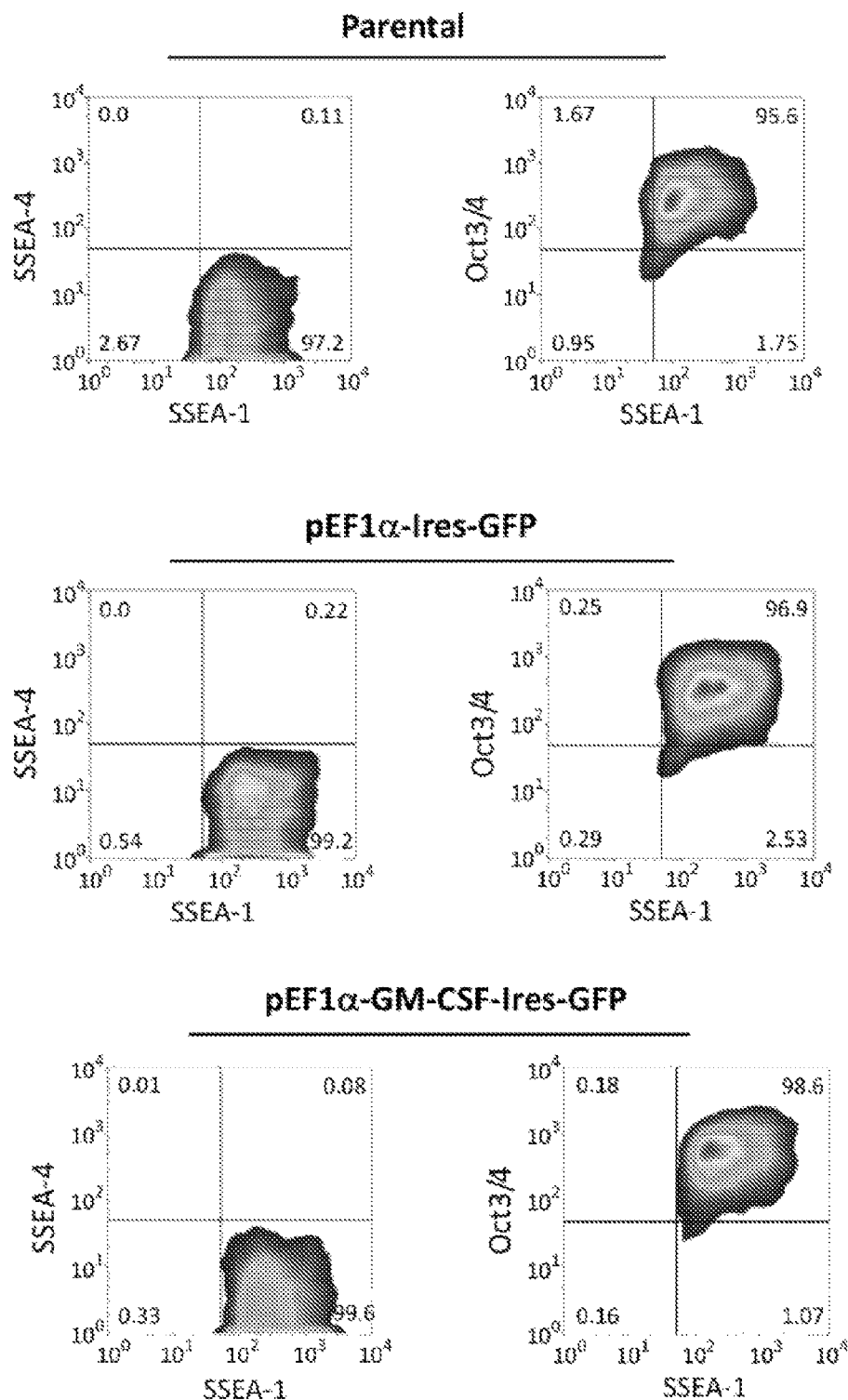

Earlier efforts to overexpress GM-CSF in murine ESCs by retroviral infection were largely unsuccessful, probably due to transcriptional suppression of endogenous and exogenous retroviruses in those cells (Schlesinger et al., 2013). Previous studies have demonstrated that the cellular elongation factor-1α (EF1α) promoter efficiently drives exogenous gene expression in murine ESCs (Chung et al., 2002; Mali et al., 2008). GM-CSF was stably expressed GM-CSF in ES-D3 cells by transfection. The vector employed in these experiments is depicted in FIG. 1A. As shown in FIG. 1B, the amounts of GM-CSF generated by ES-D3 cells expressing this vector are roughly equivalent to those generated by the STO fibroblasts employed in earlier experiments (Yaddanapudi et al., 2012). To ensure that transfection with the vectors had no effect on "stemness" (pluripotency) of ES-D3 cells, we assessed cellular expression of stem cell-associated markers SSEA-1, SSEA-4 and Oct-3/4. As shown in FIG. 1C, high levels of Oct 3/4 and SSEA-1 expression were unchanged in GM-CSF-over-expressing-cells relative to those in the vector control cells, and SSEA-4 expression remained at low levels.

Example 2

Characterization of Exosomes Isolated from GM-CSF-Expressing Murine Embryonic Stem Cells (ESCs)

Figure 2A:
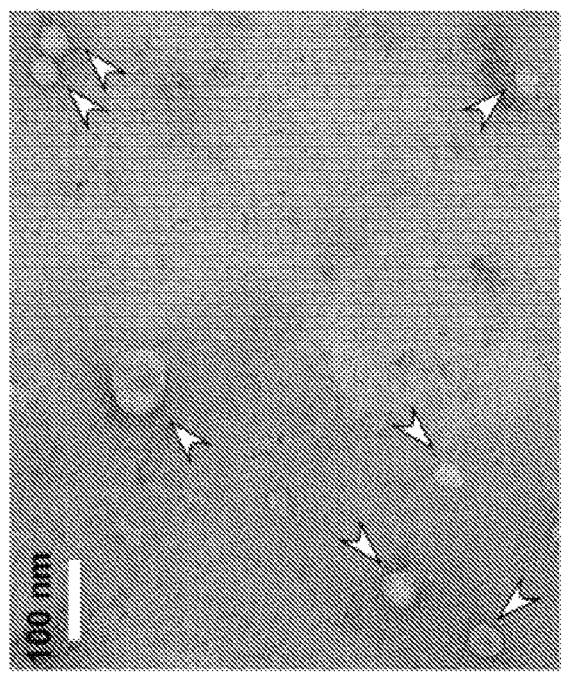
Figure 2A:
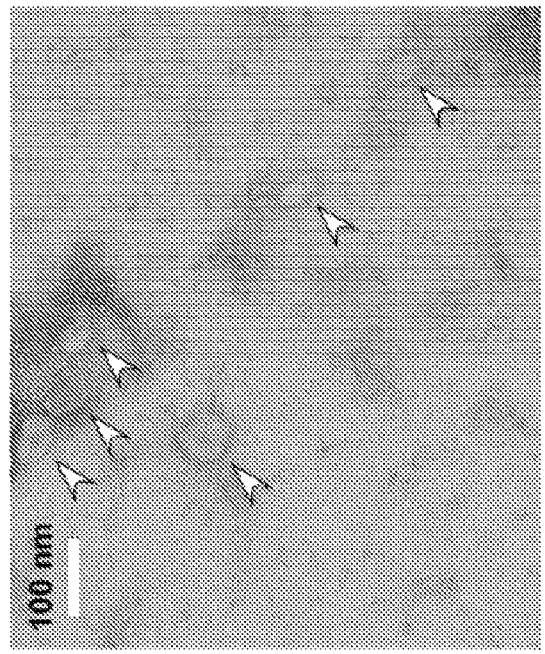
Figure 2C:
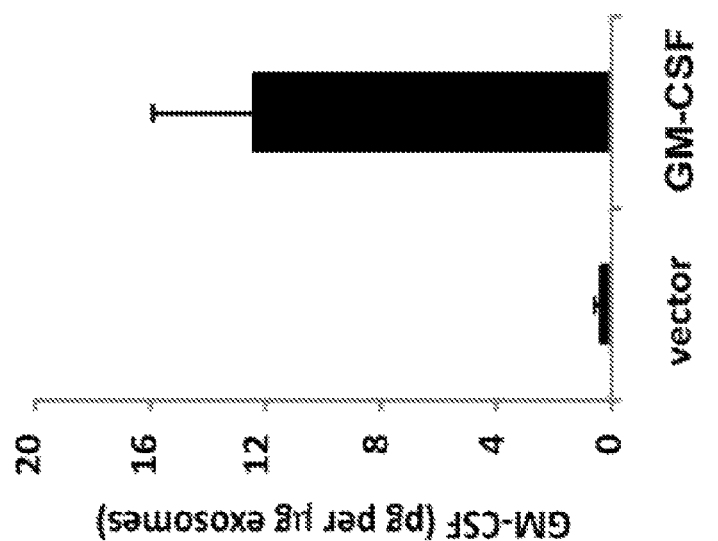
Figure 2B:
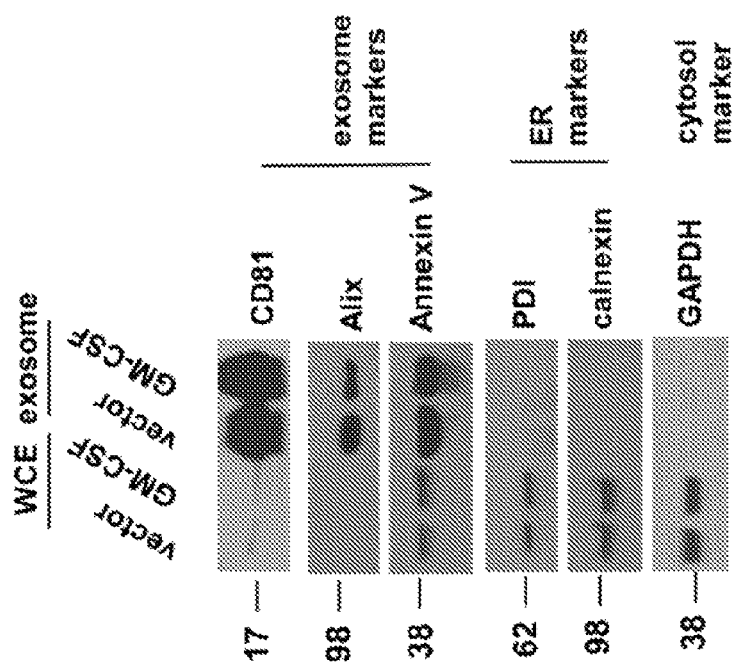

Exosomes generated by vector control cells and GM-CSF transfected cells were isolated and examined by transmission electron microscopy (TEM; FIG. 2A). Note that this was comprised of exosomes of varying sizes including individual exosomes (arrows) which is commonly observed in exosomal preparations (Thery et al., 2002; Bosch et al., 2016). Purity of exosomal material was indicated by positive western blot staining for the exosomal markers CD81, Alix, and annexin V, and a lack of endoplasmic reticulum markers protein disulfide isomerase (PDI) and calnexin and the cytosolic marker GAPDH (FIG. 2B).

To determine the presence of proteins in exosomes of ES-D3 cells, we systematically analyzed the profile of exosomal proteins by a proteomic approach. As expected, well-known exosomal protein markers, such as annexin V and Alix, were discovered to present in exosomal samples of ES-D3 cells (Table 1; see also Mignot et al., 2006). Importantly, or antigens identified in a variety of tumor types were also localized in exosomes of ES-D3 cells (Komnberg & Polliack, 1980; Glas et al., 2003; Patriarca et al., 2012; Gutschner et al., 2014), which is in agreement with the idea that embryos and tumors share similar antigens (Stonehill & Bendich, 1970; Baldwin et al., 1972a; Baldwin et al., 1972b).

TABLE 1

List of Exosome Markers and Tumor Antigens Expressed in ES-exosomes Identified Using a Proteomics Approach

| Category | Protein Name | Tumor Type |
|---|---|---|
| Exosome marker | Programmed cell death 6-interacting protein/Alix | N/A |
| Exosome marker | Annexin II | N/A |
| Exosome marker | Annexin V | N/A |
| Exosome marker | CD9 | N/A |
| Exosome marker | Transferrin receptor/CD71 | N/A |
| Exosome marker | Lysosome-associated membrane glycoprotein 1 (LAMP 1) | N/A |
| Exosome marker | Tumor susceptibility gene 101 (TSG101) | N/A |
| Exosome marker | CD81 | N/A |
| Tumor antigen | Alpha-fetoprotein | Hepatocellular carcinoma; germ cell tumors |
| Tumor antigen | Lactate dehydrogenase (LDH) | Germ cell tumor; lymphoma; leukemia |
| Tumor antigen | Fibrinogen | Bladder, ovary, and colon tumors |
| Tumor antigen | Epithelial cell adhesion molecule (EpCAM)/CD326 | Epithelial tumors |
| Tumor antigen | Cluster of differentiation 151/CD151 | Skin squamous cell carcinoma |
| Tumor antigen | Insulin-like growth factor 2 mRNA-binding | Hepatocellular carcinoma |
| Tumor antigen | Ephrin type-A receptor 2 (EPHA2) | Breast, prostate, bladder, skin, lung, ovary, and brain tumors |

It appears that almost all GM-CSF is within the exosomal preparation. As shown in FIGS. 2C and 2D, GM-CSF in these preparations was protected from digestion by proteinase K while the exosomal markers were completely digested (FIG. 2E). Therefore, to the extent that this material is an effective immunogen (vide infra), the immunologic activation by GM-CSF likely arises from exosomal fusion with the plasma membrane of antigen presenting cells.

Example 3

Figure 3A:
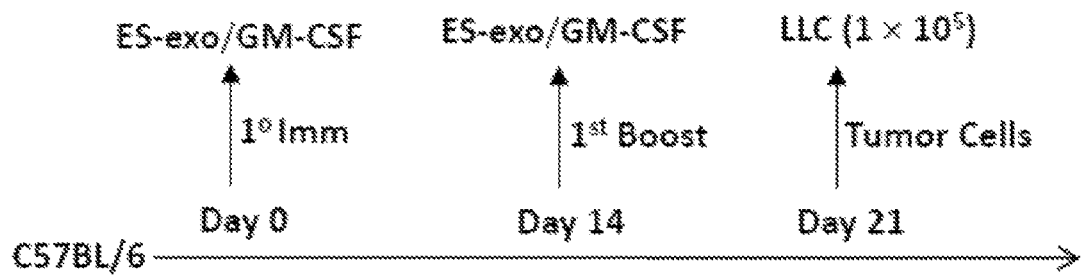
FIGS. 3A-3C depict a scheme for and the results of experiments related to assessing the ability of an exemplary ESC-derived exosome vaccination to prevent the outgrowth of an implanted lung adenocarcinoma cells (Lewis Lung Carcinoma (LLC) cells).
Figure 3B:
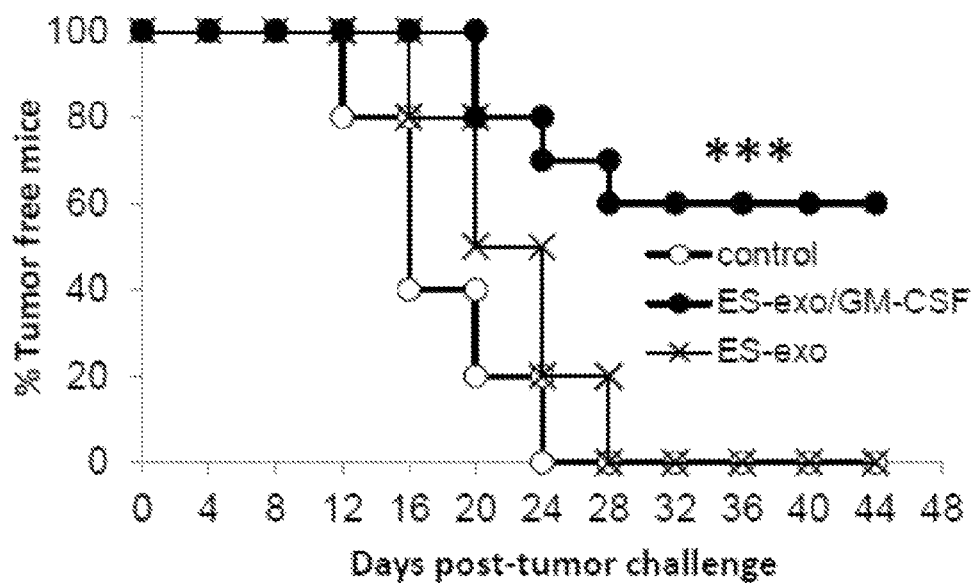
Figure 3C:
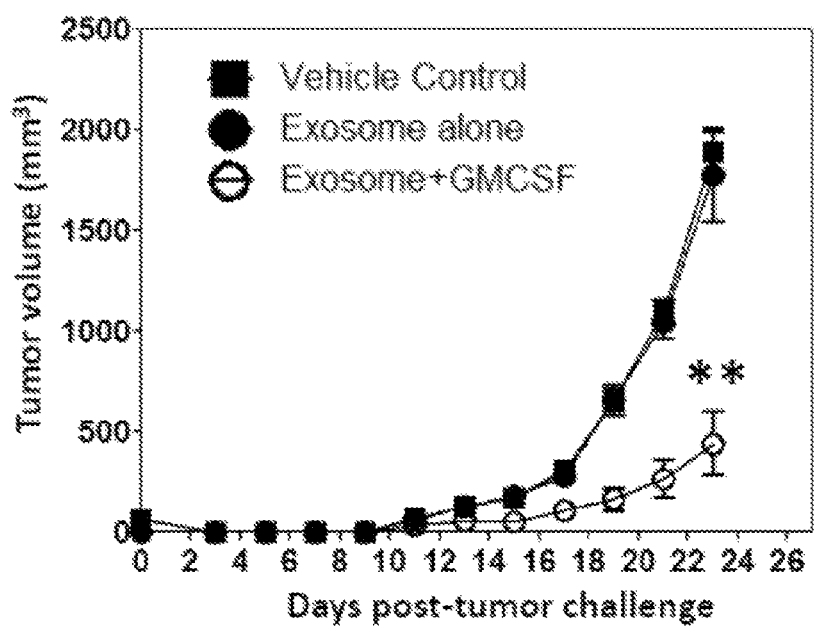

Vaccination with Exosomes Prepared from GM-CSF-Expressing ESCs Prevented the Outgrowth of an Implanted Lung Adenocarcinoma Using a standard vaccination timing regimen (FIG. 3A), C57BL/6 mice (n=10) were immunized twice (days 0 and 7) with HBSS (control), exosomes alone (ES-exo), or GM-CSF expressing exosomes (ES-exo/GM-CSF). Mice were then challenged with s.c. inoculation of LLC (day 14) and monitored for tumor outgrowth as a function of time. As shown in FIG. 3B, vaccination of mice with ES-exo/GM-CSF was 60% effective in preventing tumor outgrowth whereas all non-vaccinated control animals had developed palpable tumors by day 24 post-challenge. More importantly, those LLC tumors that did develop in exosome-GM-CSF vaccinated mice (n=8) were significantly smaller and tumor growth rate was greatly reduced compared to those developing in non-vaccinated control mice (n=20; FIG. 3C). In contrast, vaccination with control exosomes not expressing GM-CSF was completely ineffective in reducing tumor outgrowth.

Example 4

Figure 4A:
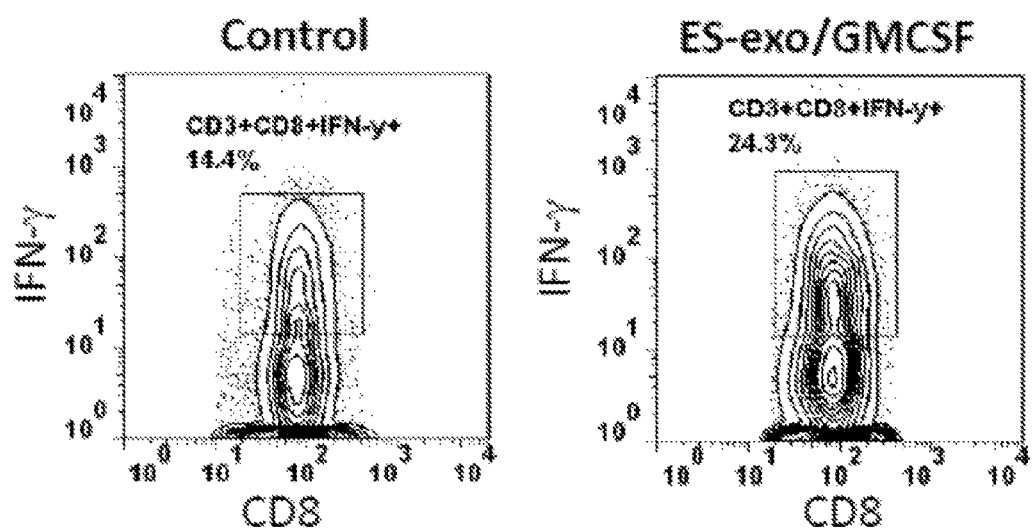
Figure 4B:
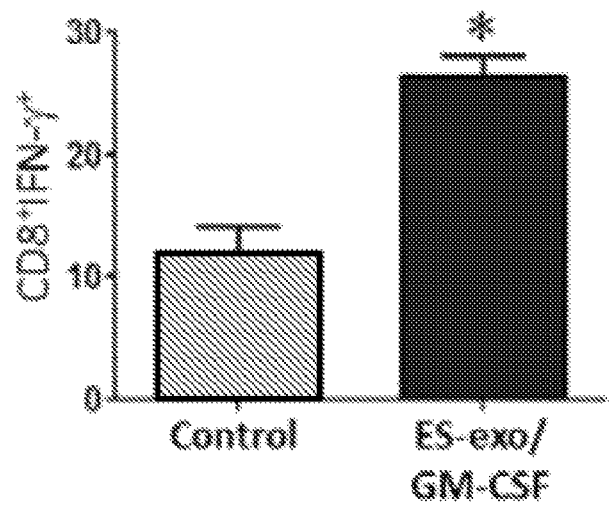
Figure 4C:
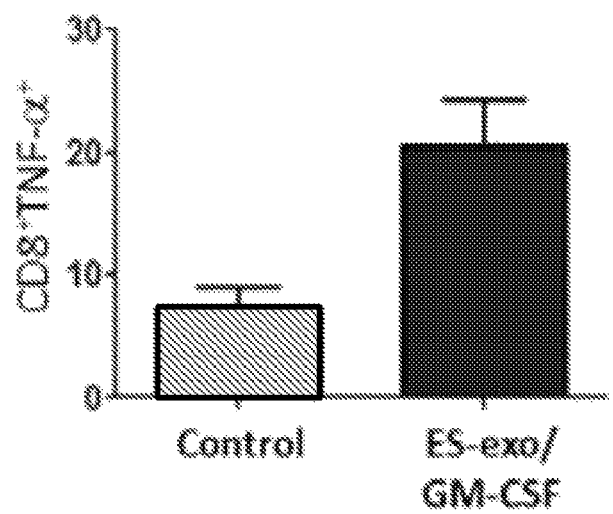

Vaccination with GM-CSF-Expressing ESC-Derived Exosomes Induced Tumor Cell-Specific Th1-Mediated Cytokine Response in $CD8^+$ T Cells The ability of $CD8^+$ T cells from vaccinated mice to produce effector cytokines required for effective anti-tumoral cytolytic activity was investigated. In response to re-stimulation with LLC cell lysate, a significantly higher frequency of IFN-γ and TNF-α producing $CD8^+$ splenocytes were obtained from ES-exo/GM-CSF vaccinated mice when compared with the non-vaccinated control group (n=4/group; t-test, p<0.05; relative to control group; FIGS. 4A-4C). In the absence of LLC re-stimulation, no increase in cytokine production was observed in $CD8^+$ splenocytes from vaccinated mice when compared to unstimulated, control non-vaccinated mice. Importantly, analysis of the phenotype of tumor-infiltrating immune cells supported the concept that vaccination led to an immune-based suppression of tumor growth. Using tumors isolated from unvaccinated and ES-exo/GM-CSF vaccinated mice, substantial increases in IFN-γ and TNF-α producing $CD8^+$ T cells were observed only in mice vaccinated with exosomes prepared from GM-CSF expressing ESCs in response to re-stimulation with PMA/ionomycin (n=4/group; t-test, p<0.05; relative to control group; FIGS. 4D-4F).

Figure 5A:
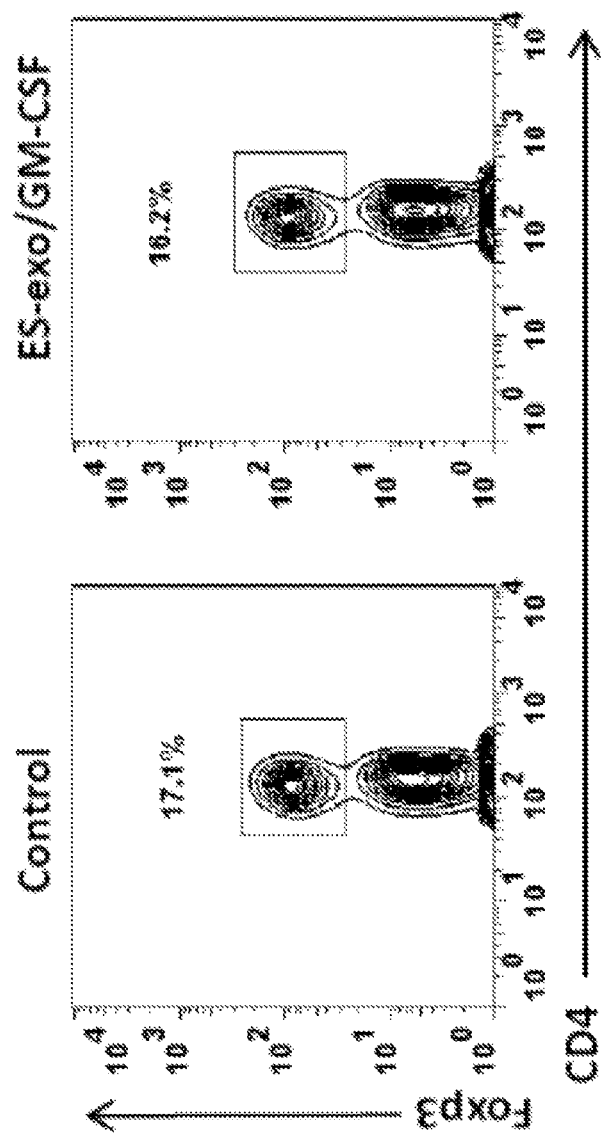
FIGS. 5A-5F depict the results of experiments demonstrating that ESC-derived exosome vaccination reduced myeloid-derived suppressor cells but did not alter T regulatory cells in the spleen. C57BL/6 mice (4 mice/group) were immunized twice (days 0 and 7) with HBSS (control), or with exosomes isolated from ES-D3 cells over-expressing GM-CSF (ES-exo/GM-CSF) in the right flank. Seven days after the last immunization, mice were challenged with $1×10^5$ LLC cells s.c. in the left flank. 18-21 days after tumor challenge, mice were euthanized, and spleens were removed. Splenocytes from vaccinated and control mice were washed, Fc receptors were blocked, and stained for surface expression of different markers and analyzed by flow cytometry.
Figure 5C:
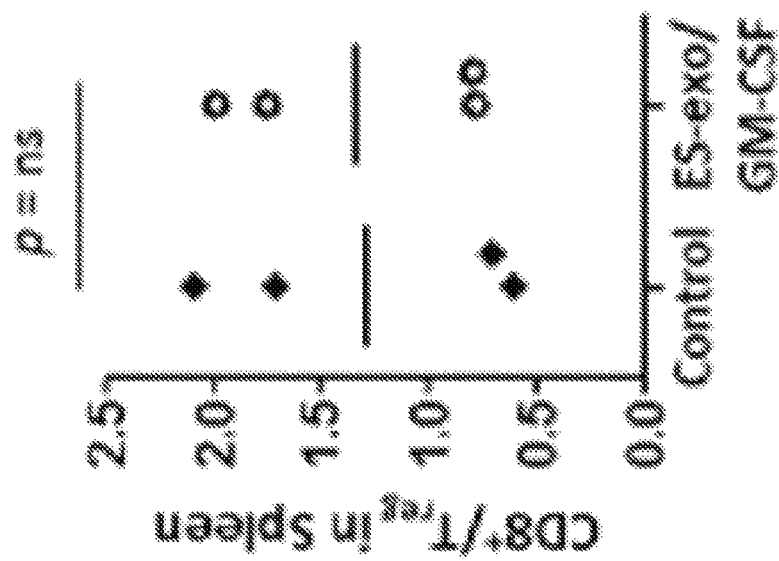
Figure 5B:
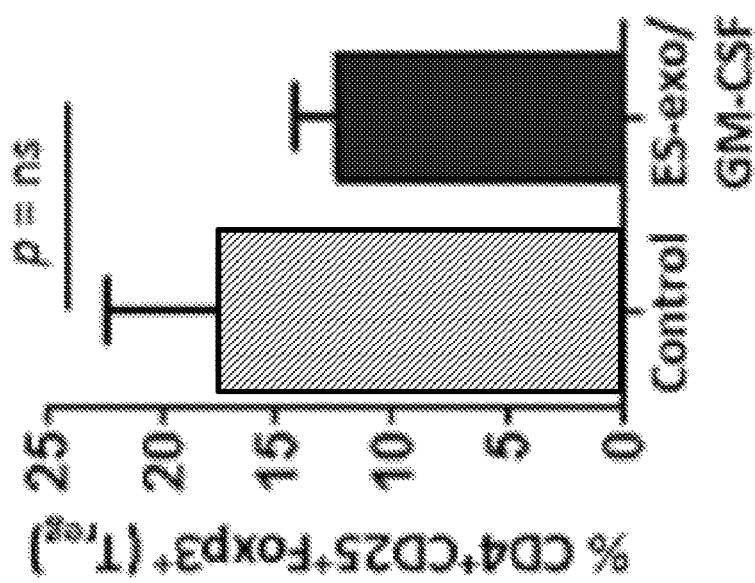
Figure 5D:
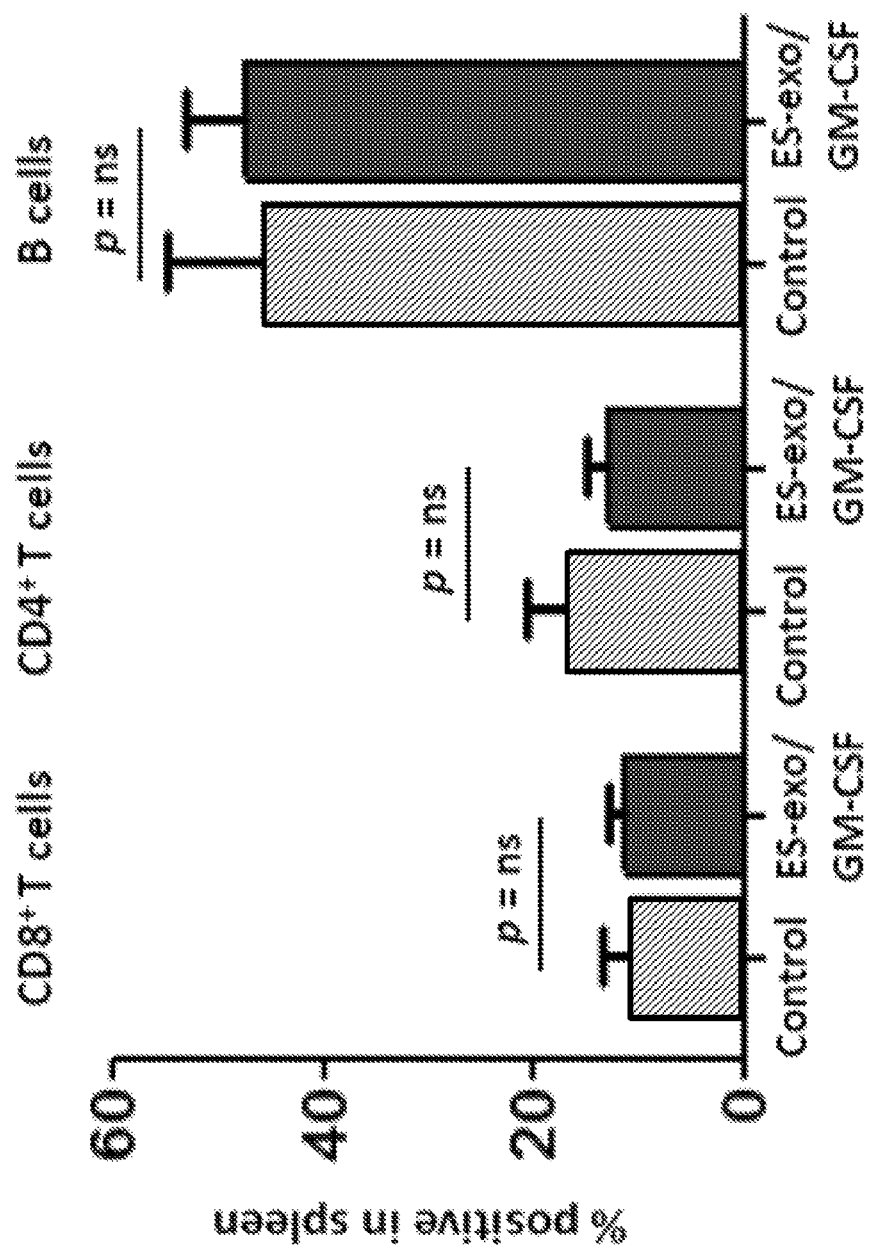
Figure 5E:
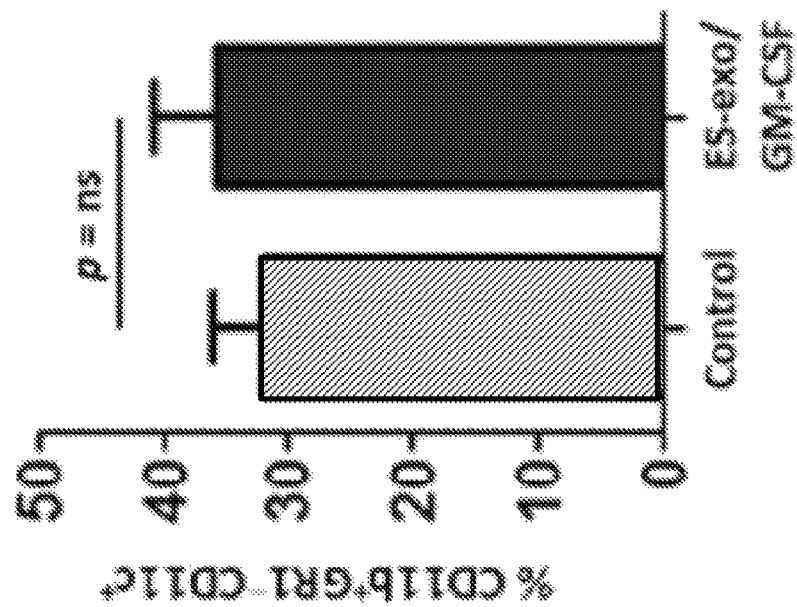
Figure 5F:
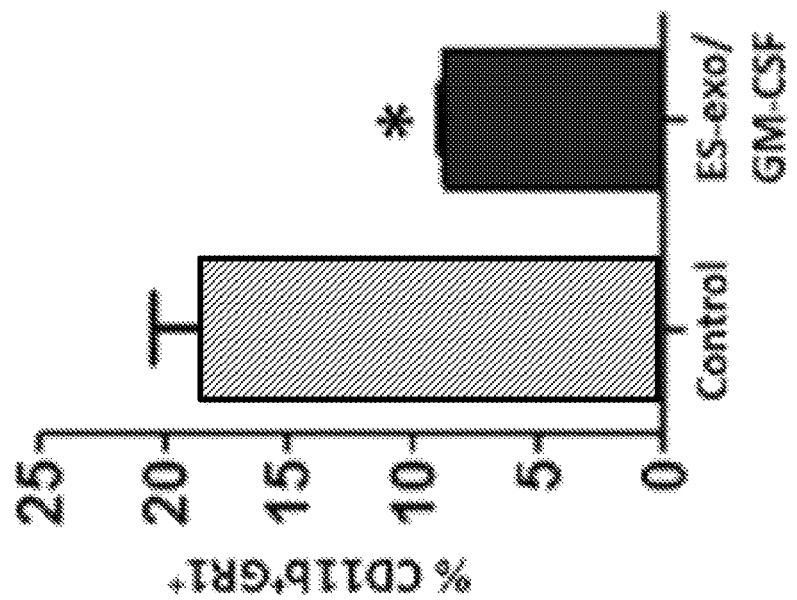

The effects of ES-exo/GM-CSF vaccination on $CD4^+$ $CD25^+Foxp3^+$ T regulatory cells ($T_{regs}$) and CD11b+Gr1+ myeloid-derived suppressor cells (MDSCs)—the two prominent suppressor populations that hamper the anti-tumoral effector responses in the spleen (Zou, 2006; Ortiz et al., 2015; Chesney et al., 2017)—were also analyzed. The data showed that the vaccination strategy employed did not reduce the percentages of splenic Tregs (FIGS. 5A, 5B) or induce any change in the ratio of $CD8^+$ T cells to $T_{regs}$ in the spleen (FIG. 5C). Also, no significant differences in the percentages of $CD4^+$ and $CD8^+$ T cells were observed (FIG. 5D) or in their absolute number in the spleens from vaccinated and control non-vaccinated mice. The percentage of MDSCs, however, was significantly decreased in the spleens of mice vaccinated with ES-exo/GM-CSF and challenged with LLC cells when compared with non-vaccinated, LLC challenged control mice (n=4/group; t test, p<0.05; relative to control group; FIG. 5E) but there were no significant differences in the percentages of splenic $CD11b^+Gr-1^-$ $CD11c^+$ dendritic cells (FIG. 5F), and $CD11b^+Gr-1^-F4-80^+$ macrophages between control and vaccinated groups.

Example 5

Figure 6A:
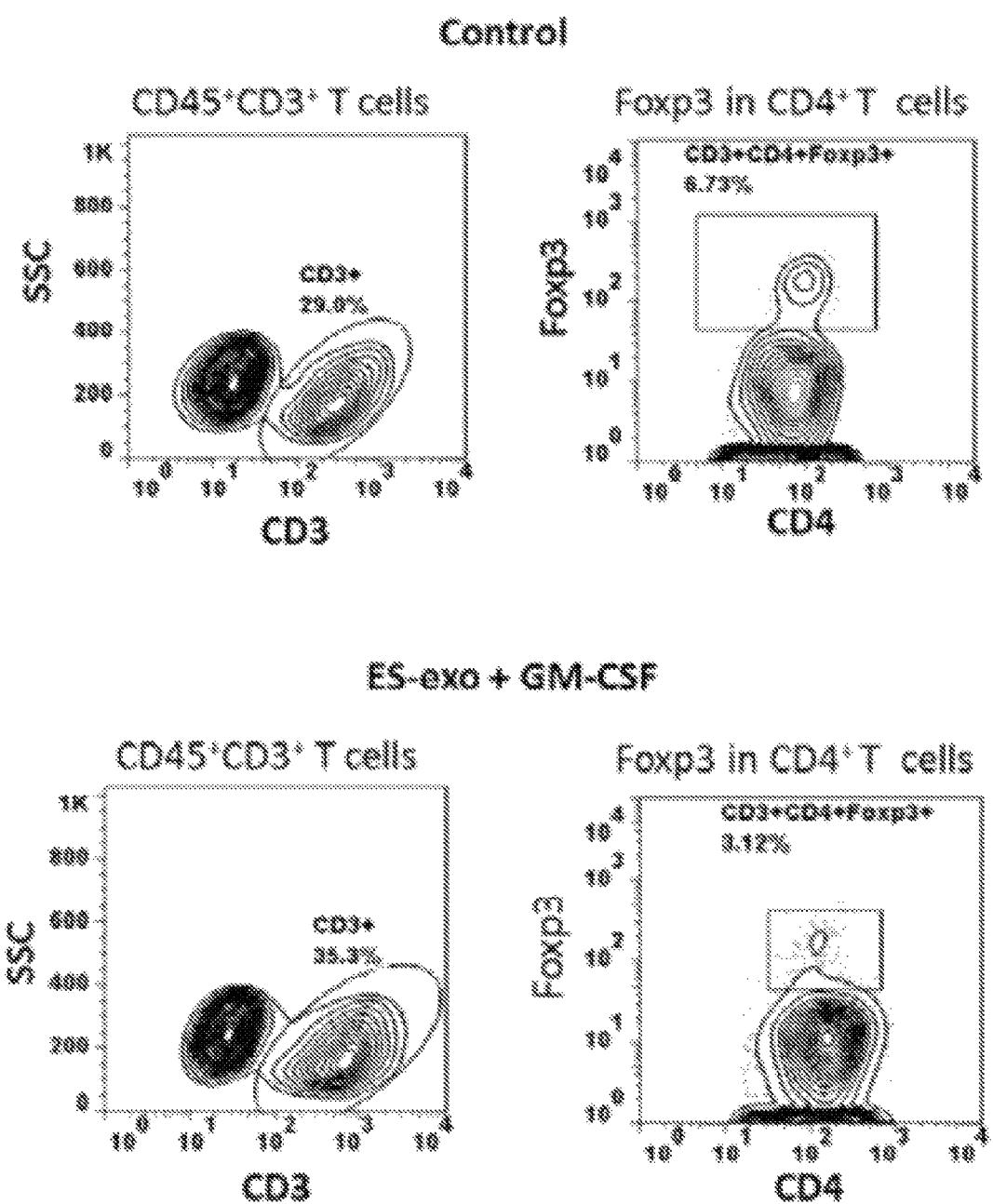
FIGS. 6A-6G show the results of experiments demonstrating that ESC-derived exosome vaccination decreased T regulatory ($T_{reg}$) cells and increased the ratio of effector $CD8^+$ T cells to $T_{reg}$ in the tumors. C57BL/6 mice (4 mice/group) were immunized twice (days 0 and 7) with HBSS (control), or with exosomes isolated from ES-D3 cells over-expressing GM-CSF (ES-exo/GM-CSF) in the right flank. Seven days after the last immunization, mice were challenged with $1×10^5$ LLC cells s.c. in the left flank. 18-21 days after tumor challenge, mice were euthanized and tumor-infiltrating cells were harvested from control and vaccinated mice and analyzed by flow cytometry.
Figure 6B:
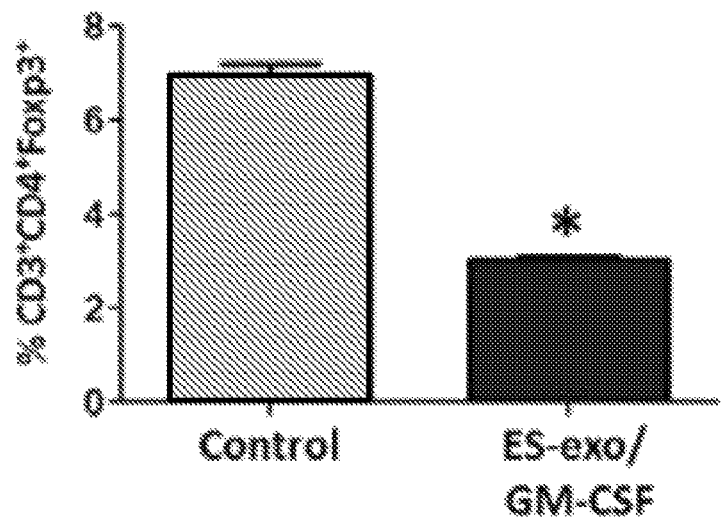
Figure 6C:
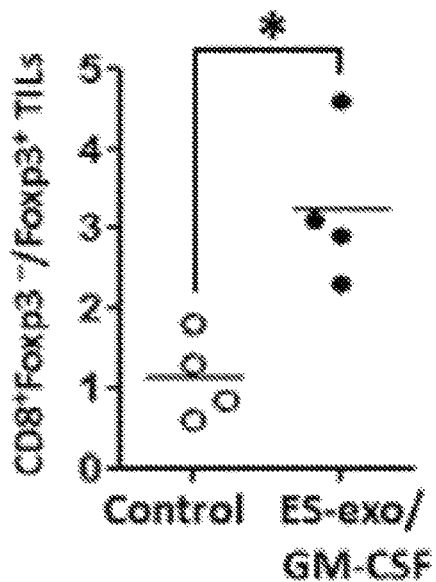
Figure 6D:
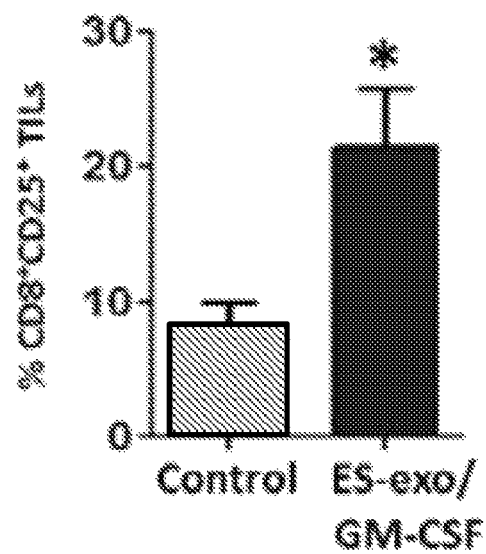

Vaccination with GMCSF-Expressing ESC-Derived Exosomes Increased the Ratio of CD8$^+$ T Effector Cells to T$_{regs}$ in Tumors The results disclosed thus far suggested that the ES-exo/GM-CSF vaccine-induced anti-tumor efficacy was reliant on the CD8$^+$ T effector cells. The effects of the employed vaccination strategy on the phenotype of tumor-infiltrating CD8$^+$ T cells, T$_{regs}$, and myeloid cells was also investigated. Tumors from controls and vaccinated mice (from the small numbers of ES-exo/GM-CSF vaccinated mice that did develop LLC lesions) were harvested and used to investigate the subset profiles of tumor-infiltrating immune cells. Flow cytometry analysis showed a significant decrease in the percentage of CD4$^+$CD25$^+$Foxp3$^+$ T$_{regs}$ in tumor infiltrates from vaccinated mice when compared with non-vaccinated control mice (n=4/group; t test, p<0.05; relative to control group; FIGS. 6A, 6B). Of equal importance, the ratio of CD8$^+$ T cells to T$_{regs}$ was significantly increased in the tumor infiltrates from ES-exo/GM-CSF vaccinated mice (n=4/group; t test, p<0.05; relative to control group; FIG. 6C). Additionally, CD8$^+$ cells in the ES-exo/GM-CSF tumor infiltrates had significantly elevated expression of the activation marker CD25 (n=4/group; t test, p<0.05; relative to control group; FIG. 6D).

Figure 6E:
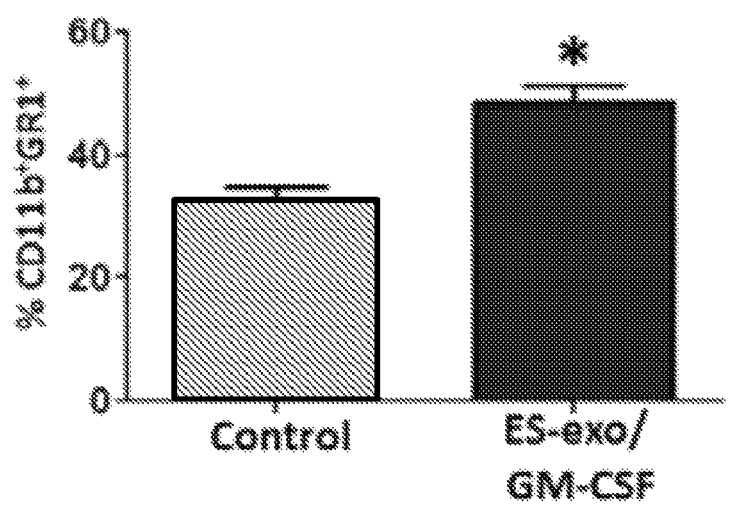
Figure 6F:
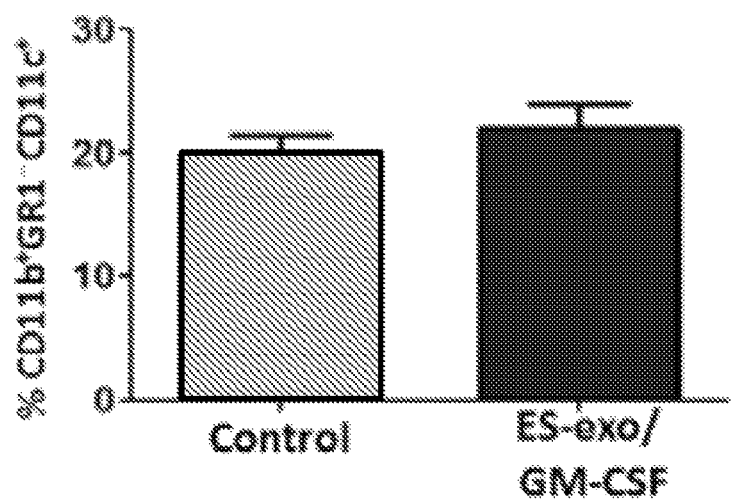
Figure 6G:
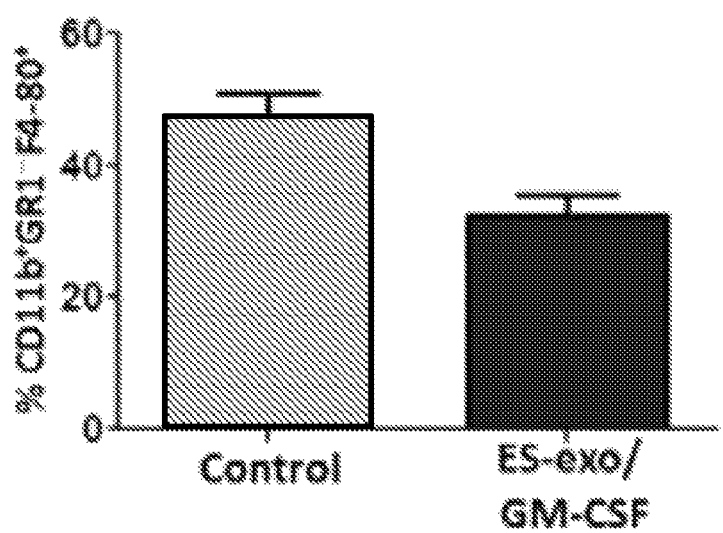

Additionally, a significant increase in the percentages of CD11b$^+$Gr-1$^+$ MDSCs was observed in tumors from ES-exo/GM-CSF vaccinated mice (n=4/group; t test, p<0.05; relative to control group; FIG. 6E) but there were no significant differences in the percentages of tumor-infiltrating CD11b$^+$Gr-1$^-$CD11c$^+$ dendritic cells, and CD11b$^+$Gr-1$^-$F4-80$^+$ macrophages between control and vaccinated groups (FIGS. 6F and 6G). This could reflect GM-CSF-mediated generation or attraction of MDSCs to the tumors (Filipazzi et al. 2007; Sawanobori et al. 2008; Morales et al., 2010; 27-29).

Example 6

Identifying Cross-Reactive Lung Tumor Antigens Using ES-Exo and Luna Tumors

Since the anti-tumor activity of the vaccine can depend on the ES-induced recognition of relevant antigens expressed in a given tumor or tumor type, the cross-reactive lung tumor antigens are explored using ES-exo and lung tumors. These studies employ a high throughput proteomics-based screening platform in combination with mass spectrometry techniques to identify common antigens expressed in ES-derived exosomes and lung tumors. Recent reports by Dr. Tuohy's group showed that targeting of the extracellular domain of anti-Mullerian hormone receptor II (AMHR2-ED) and α-lactalbumin are effective strategies for immunoprevention of ovarian cancer and breast cancer, respectively (Jaini et al., 2010; Mazumder et al., 2017; Shoemaker & Forsthuber, 2017). These so-called "retired antigens" are required for tissue-specific functions and their expression decreases with aging. Similar to testis-associated antigens (e.g., NY-ESO-1), both AMHR2-ED and α-lactalbumin antigens are overexpressed in cancer cells but show limited expression in normal tissues and hence form appealing targets for cancer vaccine development with minimal risk for inducing autoimmunity (Jaini et al., 2010; Mazumder et al., 2017; Shoemaker & Forsthuber, 2017).

Finally, a recent publication by supports the approaches disclosed herein (Kooreman et al., 2018), although those investigators employed iPSCs and a different adjuvant (CpG). These recent studies lend further credence to the concept that embryonic material can be an effective vaccine source which targets the "other" neoantigens.

DISCUSSION OF THE EXAMPLES

Vaccines have vastly improved human welfare and longevity and led to the disappearance of smallpox and near-eradication of polio. These anti-bacterial and anti-viral vaccines are most often polyvalent, prepared from killed or attenuated organisms. Polyvalency may partially explain the effectiveness of these vaccines. In fact, truly positive results with a long-sought vaccine against malaria have been reported only with *Plasmodium falciparum* sporozoite preparations (Mordmuller et al., 2017). By contrast, most attempts to use monovalent vaccines as therapy or prophylaxis for various cancers have met with very limited success, such as but not limited to the failure of Sipuleucel-T, a monovalent vaccine composed of a GM-CSF/prostatic acid phosphatase fusion, to provide significant improvements in overall survival of patients with prostate cancer (Kantoff et al., 2010).

The current attempts to generate a prophylactic vaccine for cancer prevention were based in part on observations of antigenic similarities between embryos and cancers (so-called "carcinoembryonic" antigens. As reviewed in an earlier publication (Brewer et al., 2009), a large number of such shared antigens have been identified. Previous studies demonstrated that undifferentiated, pluripotent ESCs delay tumor growth in implantable mouse models of transplantable colon carcinoma and lung cancer (Li et al., 2009; Dong et al., 2010). These reports corroborate previous data that indicated that vaccination with irradiated, allogeneic murine ESC along with allogeneic fibroblasts expressing GM-CSF as an immunostimulatory adjuvant was 70-100% effective in preventing both implantable and carcinogen-induced lung adenocarcinomas without detectable toxicity or signs of autoimmunity (Li, et al., 2009; Yaddanapudi et al., 2012).

Reported herein is that exosomes derived from GM-CSF-expressing murine ESCs can be used as a vaccine for the prevention of tumor outgrowth. In those animals that developed tumors, tumor growth was significantly slowed compared to unvaccinated control animals and those vaccinated with exosomes from ESCs which do not express GM-CSF. In the latter group of animals, tumor outgrowth did not differ from that seen in unvaccinated mice. These observations are in agreement with earlier reports of the potency of GM-CSF as an immune stimulant (reviewed in Dranoff, 2002). Indeed, this property has been recently exploited by Bencherif and co-workers for amplification of immune responses in a melanoma model (Bencherif et al., 2015). In the experimental tumor model disclosed herein, ES-exo/GM-CSF combination vaccine significantly increased the ratio of CD8$^+$ T cells to T$_{regs}$, and the percentages of CD8$^+$CD25$^+$ and CD8$^+$IFN-γ$^+$ effector cells within the tumors that is indicative of effective vaccine-induced, tumor-reactive immune system priming. These immunophenotyping data also lend additional support to the conclusion that such vaccination could be a viable approach to the prevention of cancers in humans.

Exosomes are thus promising agents for immunotherapy of cancer. The exosome-based anti-cancer therapies harness their high stability, in vivo bioavailability, and inherent ability to stimulate anti-tumor immune responses. The use of tumor-derived exosomes as a vaccine has been proposed earlier (reviewed in Kunigelis & Graner, 2015), although that approach is complicated by the fact that such preparations can be strongly immunosuppressive. Furthermore, the idea of using tumors expressing GM-CSF as a therapeutic vaccine has been explored by others (Dranoff et al., 1993; Borrello & Pardoll, 2002) with variable success in particular animal models. In pre-clinical studies, exosomes obtained from matured dendritic cells (DCs) expressed more abundant MHC-I and MHC-II molecules as well as co-stimulatory molecules (e.g., CD40, CD80, and CD86) and induced potent antigen-specific anti-tumor T effector responses shown by CTL and NK cells both in vitro and in vivo (Raposo et al., 1996; Zitvogel et al., 1998; Thery et al., 1999; Viaud et al., 2009). Similarly, ES-exo are stable vesicles harboring protein contents that can be tailor-manufactured from human cell lines in clinical grade (cGMP) quality (Thery et al., 2002; Chaput et al., 2005). Furthermore, ES-exo can be produced in large quantities and cryo-preserved for more than 6 months at −80° C. with both phenotype and function intact.

A strength of the presently disclosed approach appears to reside in the fact that this it employs a polyvalent vaccine which can lead to immune recognition of a number of antigens shared by early embryos and tumors. The preliminary proteomics studies described herein (see Table 1) suggested that ESC-derived exosomes harbor multiple tumor antigens (e.g., Alpha-fetoprotein, CD151). Based on the strong in vivo anti-tumor T cell effector responses that were observed with this vaccine, it is very likely that at least one or more of the tumor-cell expressed embryonal antigens is involved in eliciting anti-tumor immune responses.

REFERENCES

All references cited in the instant disclosure, including but not limited to all patents, patent applications and publications thereof, scientific journal articles, and database entries (e.g., GENBANK® biosequence database entries and all annotations available therein) are incorporated herein by reference in their entireties to the extent that they supplement, explain, provide a background for, or teach methodology, techniques, and/or compositions employed herein.

Altschul et al. (1990) Basic local alignment search tool. J Mol Biol 215:403-410.

Ausubel et al. (1992) *Current Protocols in Molecular Biology*, John Wylie & Sons, Inc., New York, N.Y., United States of America.

Baldwin et al. (1972a) Embryonic Antigen Expression in Chemically Induced Rat Hepatomas and Sarcomas. Int J Cancer 10:233-243.

Baldwin et al. (1972b) Tumor Specific and Embryonic Antigen Expression on Chemically Induced Rat Tumors. Ann I Pasteur Paris 122:715-728.

Bencherif et al. (2015) Injectable cryogel-based whole-cell cancer vaccines. Nat Commun 6:7556.

Borrello & Pardoll (2002) GM-CSF-based cellular vaccines: a review of the clinical experience. Cytokine Growth Factor Rev 13:185-193.

Bosch et al. (2016) Trehalose prevents aggregation of exosomes and cryodamage. Sci Reports 6:36162.

Brewer et al. (2009) Embryonic vaccines against cancer: An early history. Exp Mol Pathol 86:192-197.

Chaput et al. (2005) The potential of exosomes in immunotherapy. Expert Opin Biol Ther 5:737-747.

Chesney et al. (2017) Mycloid-derived suppressor cells—a new therapeutic target to overcome resistance to cancer immunotherapy. J Leukoc Biol 102:727-740.

Chung et al. (2002) Genetic engineering of mouse embryonic stem cells by Nurr1 enhances differentiation and maturation into dopaminergic neurons. Eur J Neurosci 16:1829-1838.

Colombo et al. (2014) Biogenesis, secretion, and intercellular interactions of exosomes and other extracellular vesicles. Annu Rev Cell Dev Biol 30:255-289.

Dong et al. (2010) Administration of embryonic stem cells generates effective antitumor immunity in mice with minor and heavy tumor load. Cancer Immunol Immun 59:1697-1705.

Dranoff (2002) GM-CSF-based cancer vaccines. Immunol Rev 188:147-154.

Dranoff et al. (1993) Vaccination with Irradiated Tumor-Cells Engineered to Secrete Murine Granulocyte-Macrophage Colony-Stimulating Factor Stimulates Potent, Specific, and Long-Lasting Antitumor Immunity. Proc Natl Acad Sci USA 90:3539-3543.

Evans et al. (1981) Establishment in culture of pluripotential cells from mouse embryos. Nature 292:154-156.

Filipazzi et al. (2007) Identification of a new subset of myeloid suppressor cells in peripheral blood of melanoma patients with modulation by a granulocyte-macrophage colony-stimulation factor based antitumor vaccine. J Clin Oncol 25:2546-2553.

Gabrilovich & Nagaraj (2009) Myeloid-derived suppressor cells as regulators of the immune system. Nat Rev Immunol 9:162-174.

Gehrmann et al. (2014) Harnessing the exosome-induced immune response for cancer immunotherapy. Semin Cancer Biol 28:58-67.

Glas et al. (2003) Tumor markers in the diagnosis of primary bladder cancer. A systematic review. J Urology 169:1975-1982.

Gutschner et al. (2014) Insulin-Like Growth Factor 2 mRNA-Binding Protein 1 (IGF2BP1) Is an Important Protumorigenic Factor in Hepatocellular Carcinoma. Hepatology 59:1900-1911.

Henikoff & Henikoff (1989) Proc Natl Acad Sci USA 89:10915-10919.

Jaini et al. (2010) An autoimmune-mediated strategy for prophylactic breast cancer vaccination. Nat Med 16:799-803.

Kantoff et al. (2010) Sipuleucel-T immunotherapy for castration-resistant prostate cancer. N Engl J Med 363:411-422.

Karlin & Altschul (1993) Applications and statistics for multiple high-scoring segments in molecular sequences. Proc Natl Acad Sci USA 90:5873-5887.

Kooreman et al. (2018) Autologous iPSC-Based Vaccines Elicit Anti-tumor Responses In Vivo. Cell Stem Cell 22:501-513.

Komberg & Polliack (1980) Serum Lactic-Dehydrogenase (Ldh) Levels in Acute-Leukemia—Marked Elevations in Lymphoblastic-Leukemia. Blood 56:351-355.

Kunigelis & Graner (2015) The Dichotomy of Tumor Exosomes (TEX) in Cancer Immunity: Is It All in the ConTEXt? Vaccines 3:1019-1051.

Li et al. (2004) Isolation and culture of pluripotent cells from in vitro produced porcine embryos. Zygote 12:43-48.

Li et al. (2009) Vaccination with Human Pluripotent Stem Cells Generates a Broad Spectrum of Immunological and Clinical Responses Against Colon Cancer. Stem Cells 27:3103-3111.

Loo & Cotman (1998) in *Cell Biology: A Laboratory Handbook* (J. E. Celis, ed.) Vol. 1, pages 65-72, Academic Press, San Diego, Calif., United States of America.

Mali et al. (2008) Improved efficiency and pace of generating induced pluripotent stem cells from human adult and fetal fibroblasts. Stem Cells 26:1998-2005.

Martin (1981) Isolation of a pluripotent cell line from early mouse embryos cultured in medium conditioned by teratocarcinoma stem cells. Proc Natl Acad Sci USA 78:7634-7638.

Matsui et al. (1991) Effect of Steel factor and leukaemia inhibitory factor on murine primordial germ cells in culture. Nature 353:750-751.

Mazumder et al. (2017) Primary Immunoprevention of Epithelial Ovarian Carcinoma by Vaccination against the Extracellular Domain of Anti-Mullerian Hormone Receptor II. Cancer Prev Res (Phila) 10:612-624.

McMahon & Bradley (1990) The Wnt-1 (int-1) proto-oncogene is required for development of a large region of the mouse brain. Cell 62:1073-1085.

Mignot et al. (2006) Prospects for exosomes in immunotherapy of cancer. J Cell Mol Med 10:376-388.

Morales et al. (2010) GM-CSF is one of the main breast tumor-derived soluble factors involved in the differentiation of CD11b-Gr1-bone marrow progenitor cells into myeloid-derived suppressor cells. Breast Cancer Res Tr 123:39-49.

Mordmuller et al. (2017) Sterile protection against human malaria by chemoattenuated PfSPZ vaccine. Nature 542:445-449.

Nagy et al. (1990) Embryonic stem cells alone are able to support fetal development in the mouse. Development 110:815-821.

Nakagawa et al. (2008) Generation of induced pluripotent stem cells without Myc from mouse and human fibroblasts. Nat Biotechnol 26:101-106.

Needleman & Wunsch (1970) A general method applicable to the search for similarities in the amino acid sequence of two proteins. J Mol Biol 48:443-453.

Nims et al. (2010) Short tandem repeat profiling: part of an overall strategy for reducing the frequency of cell misidentification. In Vitro Cell Dev Biol Anim 46: 811-819.

Ortiz et al. (2015) Myeloid-derived suppressor cells in the development of lung cancer. Cancer Immunol Res 2:50-58.

Patriarca et al. (2012) Epithelial cell adhesion molecule expression (CD326) in cancer: A short review. Cancer Treat Rev 38:68-75.

PCT International Patent Application Publication Nos. WO 0999/053021; WO 2005/080598; WO 2007/069666; WO 2008/118820.

Pearson & Lipman (1988) Improved tools for biological sequence comparison. Proc Natl Acad Sci USA 85:2444-2448.

Raposo et al. (1996) B lymphocytes secrete antigen-presenting vesicles. J Exp Med 183:1161-1172.

Resnick et al. (1992) Long-term proliferation of mouse primordial germ cells in culture. Nature 359:550-551.

Robertson (1987) Teratocarcinomas and Embryonic Stem Cells: A Practical Approach IRL Press, Washington, D.C., United States of America.

Sawanobori et al. (2008) Chemokine-mediated rapid turnover of myeloid-derived suppressor cells in tumor-bearing mice. Blood 111:5457-5466.

Schlesinger et al. (2013) Proviral Silencing in Embryonic Cells Is Regulated by Yin Yang 1. Cell Rep 4:50-58.

Schone (1906) Untersuchungen uber Karzinomimmunität bei Mausen. Münchener Medizinische Wochenschrift 51:2517-2519.

Shamblott et al. (1998) Derivation of pluripotent stem cells from cultured human primordial germ cells. Proc Natl Acad Sci USA 95:13726-13731.

Shoemaker & Forsthuber (2017) Targeting "Retired Antigens" for Cancer Immunoprevention. Cancer Prev Res (Phila) 10:607-608.

Smith & Waterman (1981) Comparison of biosequences Adv Appl Math 2:482-489.

Stonehill & Bendich (1970) Retrogenetic Expression—Reappearance of Embryonal Antigens in Cancer Cells. Nature 228:370-372.

Takahashi & Yamanaka (2006). Induction of pluripotent stem cells from mouse embryonic and adult fibroblast cultures by defined factors. Cell 126:663-676.

Takahashi et al. (2007) Induction of pluripotent stem cells from adult human fibroblasts by defined factors. Cell 131:861-872.

Thery et al. (1999) Molecular characterization of dendritic cell-derived exosomes. Selective accumulation of the heat shock protein hsc73. J Cell Biol 147:599-610.

Thery et al. (2002) Exosomes: composition, biogenesis and function. Nat Rev Immunol 2:569-579.

Thomson et al. (1995) Isolation of a primate embryonic stem cell line. Proc Natl Acad Sci USA 92:7844-7844.

Thomson et al. (1996) Pluripotent cell lines derived from common marmoset (*Callithrix jacchus*) blastocysts. Biol Reprod 55:254-259.

Tucker et al. (1997) A transgenic mouse strain expressing four drug-selectable marker genes. Nucleic Acids Res 25:3745-3746.

U.S. Patent Application Publication Nos. 2005/0266553; 20060030042

U.S. Pat. Nos. 5,340,740; 5,453,357; 5,656,479; 5,670,372; 5,690,926; 5,830,510; 5,843,780; 6,011,197; 6,090,622; 6,200,806; 6,245,566; 6,271,436; 6,331,406; 6,333,192; 6,800,480; 6,875,607; 6,921,632; 7,153,684; 7,964,401; 8,048,999; 8,058,065; 8,278,104; 8,440,461; 9,279,103.

Valadi et al. (2007) Exosome-mediated transfer of mRNAs and microRNAs is a novel mechanism of genetic exchange between cells. Nat Cell Biol 9:654-659.

Viaud et al. (2009) Dendritic cell-derived exosomes promote natural killer cell activation and proliferation: a role for NKG2D ligands and IL-15Ralpha. PLoS One 4:e4942.

Williams et al. (1988) Myeloid leukaemia inhibitory factor maintains the developmental potential of embryonic stem cells. Nature 336:684-687.

Yaddanapudi et al. (2012) Vaccination with Embryonic Stem Cells Protects against Lung Cancer: Is a Broad-Spectrum Prophylactic Vaccine against Cancer Possible? Plos One 7:e42289.

Yu et al. (2007) Induced pluripotent stem cell lines derived from human somatic cells. Science 318:1917-1920.

Zitvogel et al. (1998) Eradication of established murine tumors using a novel cell-free vaccine: dendritic cell-derived exosomes. Nat Med 4:594-600.

Zou (2006) Regulatory T cells, tumour immunity and immunotherapy. Nat Rev Immunol 6:295-307.

It will be understood that various details of the presently disclosed subject matter can be changed without departing from the scope of the presently disclosed subject matter. Furthermore, the foregoing description is for the purpose of illustration only, and not for the purpose of limitation.

What is claimed is:

1. A method for preventing and/or inhibiting growth of a lung cancer or a breast cancer in a subject, the method comprising administering to the subject one or more doses of a composition comprising a plurality of exosomes generated from stem cells, optionally embryonic stem cells (ESCs), induced pluripotent stem cells (iPSCs), or a combination thereof, which have been modified to express a granulocyte-macrophage colony stimulating factor (GM-CSF) polypeptide, optionally a mammalian GM-CSF polypeptide, in an amount and via a route of administration sufficient to prevent and/or inhibit growth of the lung cancer or the breast cancer in the subject.

2. A method for preventing and/or inhibiting metastases of a lung cancer or a breast cancer in a subject in need thereof, the method comprising administering to the subject a composition as in claim 1 in an amount and via a route of administration sufficient to prevent and/or inhibit metastases of the lung cancer or the breast cancer in the subject.

3. The method of claim 1, wherein the administering is subsequent to resection of a primary tumor from the subject.

4. The method of claim 1, wherein the subject is a human.

5. The method of claim 1, further comprising treating the subject with at least one additional anti-cancer therapy, optionally wherein the at least one additional anti-cancer therapy is selected from the group consisting of radiotherapy, chemotherapy, treatment with an immune checkpoint inhibitor, immunotherapy, surgery, and combinations thereof.

6. The method of claim 5, wherein the at least one additional anti-cancer therapy is provided to the subject at a time prior to, concurrent with, subsequent to, or combinations thereof, the administering step.

7. A method for inducing an anti-tumor immune response in a subject, the method comprising administering to the subject a composition comprising one or more pharmaceutically acceptable carriers and/or excipients and a plurality of exosomes generated from stem cells that have been modified to express a granulocyte-macrophage colony stimulating factor (GM-CSF) polypeptide.

8. The method of claim 7, wherein the stem cells are embryonic stem cells (ESCs), induced pluripotent stem cells (iPSCs), or a combination thereof.

9. The method of claim 7, wherein the ESCs and/or the iPSCs are mammalian ESCs and/or iPSCs.

10. The method of claim 9, wherein the mammalian ESCs and/or iPSCs are human ESCs and/or iPSCs.

11. The method of claim 7, wherein the GM-CSF polypeptide is a mammalian GM-CSF polypeptide, optionally a human GM-CSF polypeptide or a murine GM-CSF polypeptide.

12. The method of claim 7, wherein the anti-tumor immune response is sufficient to:

(a) prevent occurrence of a tumor in the subject;
(b) delay occurrence of a tumor in the subject;
(c) reduce a rate at which a tumor develops in the subject;
(d) prevent recurrence of a tumor in the subject;
(e) suppress growth of a tumor in a subject;
(f) prevent or inhibit metastasis of a tumor in the subject; or
(g) combinations thereof.

13. The method of claim 7, wherein the anti-tumor immune response comprises a cytotoxic T cell response against an antigen present in and/or on a cell of the tumor.

14. The method of claim 7, wherein the subject is a human.

15. The method of claim 14, wherein the cytotoxic T cell response is mediated by $CD8^+$ T cells.

* * * * *